(12) United States Patent
Ehninger et al.

(10) Patent No.: US 9,867,650 B2
(45) Date of Patent: Jan. 16, 2018

(54) UNIVERSAL SELF-LIMITING ELECTROSURGICAL RETURN ELECTRODE

(71) Applicant: Megadyne Medical Products, Inc., Draper, UT (US)

(72) Inventors: Michael D. Ehninger, South Jordan, UT (US); Paul R. Borgmeier, Salt Lake City, UT (US); Melissa K. Fischer, Cumming, GA (US)

(73) Assignee: Megadyne Medical Products, Inc., Draper, UT (US)

( * ) Notice: Subject to any disclaimer, the term of this patent is extended or adjusted under 35 U.S.C. 154(b) by 406 days.

(21) Appl. No.: 14/140,800

(22) Filed: Dec. 26, 2013

(65) Prior Publication Data

US 2015/0182278 A1 Jul. 2, 2015

(51) Int. Cl.
*A61B 18/16* (2006.01)
*A61B 18/12* (2006.01)

(52) U.S. Cl.
CPC .......... *A61B 18/1233* (2013.01); *A61B 18/16* (2013.01); *A61B 2018/167* (2013.01)

(58) Field of Classification Search
CPC ..... A61B 18/16; A61B 18/162; A61B 18/167; A61B 5/6892
See application file for complete search history.

(56) References Cited

U.S. PATENT DOCUMENTS

| | | |
|---|---|---|
| 3,089,496 A | 5/1963 | Degelman |
| 3,543,760 A | 12/1970 | Bolduc |
| 3,601,126 A | 8/1971 | Estes |
| 3,720,209 A | 3/1973 | Bolduc |
| 3,848,600 A | 11/1974 | Patrick, Jr. et al. |
| 4,088,133 A | 5/1978 | Twentier |
| 4,092,985 A | 6/1978 | Kaufman |
| 4,094,320 A | 6/1978 | Newton et al. |

(Continued)

FOREIGN PATENT DOCUMENTS

| | | |
|---|---|---|
| GB | 140736 | 6/1973 |
| GB | 2052269 | 1/1981 |

(Continued)

OTHER PUBLICATIONS

International Search Report and Written Opinion for PCT/US14/72426 dated May 29, 2015.

(Continued)

*Primary Examiner* — Jaymi Della
*Assistant Examiner* — Eunhwa Kim
(74) *Attorney, Agent, or Firm* — Workman Nydegger

(57) ABSTRACT

A self-limiting electrosurgical return electrode for use with electrosurgical procedures is disclosed. The return electrode includes a conductive element and pads disposed on opposing sides of the conductive element. The conductive element, optionally in combination with the pads, is configured to limit the density of electrical current that passes from a patient to the return electrode. The conductive element and the pads can cooperate to define two separate working surfaces on opposing sides of the return electrode. The return electrode can also be safely used with patients of substantially any size and without requiring adjustments to the power settings of an electrosurgical generator.

25 Claims, 10 Drawing Sheets

(56) References Cited

U.S. PATENT DOCUMENTS

| | | |
|---|---|---|
| 4,117,846 A | 10/1978 | Williams |
| 4,166,465 A | 9/1979 | Esty et al. |
| 4,188,927 A | 2/1980 | Harris |
| 4,200,104 A | 4/1980 | Harris |
| 4,207,904 A | 6/1980 | Greene |
| 4,226,247 A | 10/1980 | Hauser et al. |
| 4,231,372 A | 11/1980 | Newton |
| 4,237,886 A | 12/1980 | Sakurada et al. |
| 4,237,887 A | 12/1980 | Gonser |
| 4,267,840 A | 5/1981 | Lazer et al. |
| 4,304,235 A | 12/1981 | Kaufman |
| 4,384,582 A | 5/1983 | Watt |
| 4,387,714 A | 6/1983 | Geddes et al. |
| 4,669,468 A | 6/1987 | Cartmell et al. |
| 4,770,173 A | 9/1988 | Feucht et al. |
| 4,799,480 A | 1/1989 | Abraham et al. |
| 4,936,842 A | 6/1990 | D'Amelio et al. |
| 5,352,315 A | 10/1994 | Carrier et al. |
| 5,354,790 A | 10/1994 | Keusch et al. |
| 5,520,683 A | 5/1996 | Subramaniam et al. |
| 5,830,212 A | 11/1998 | Cartmell et al. |
| 5,836,942 A | 11/1998 | Netherly et al. |
| 6,049,927 A | 4/2000 | Thomas |
| 6,053,910 A | 4/2000 | Fleenor |
| 6,083,221 A | 7/2000 | Fleenor et al. |
| 6,111,233 A | 8/2000 | Rock et al. |
| 6,160,246 A | 12/2000 | Rock et al. |
| 6,214,000 B1 | 4/2001 | Fleenor et al. |
| 6,389,681 B1 | 5/2002 | Rock et al. |
| 6,454,764 B1 | 9/2002 | Fleenor et al. |
| 6,544,258 B2 | 4/2003 | Fleenor et al. |
| 6,547,786 B1 | 4/2003 | Globe |
| 6,548,789 B1 | 4/2003 | Rock et al. |
| 6,582,424 B2 | 6/2003 | Fleenor et al. |
| 6,666,859 B1 | 12/2003 | Fleenor et al. |
| 6,713,733 B2 | 3/2004 | Kockman et al. |
| 6,723,967 B2 | 4/2004 | Rock et al. |
| 6,814,889 B1 | 11/2004 | O'Grady et al. |
| 6,852,956 B2 | 2/2005 | Rock et al. |
| 6,875,963 B2 | 4/2005 | Rock et al. |
| 6,963,055 B2 | 11/2005 | Rock et al. |
| 7,038,177 B2 | 5/2006 | Rock |
| 7,166,102 B2 | 1/2007 | Fleenor et al. |
| 7,202,443 B2 | 4/2007 | Rock et al. |
| 7,367,971 B2 | 5/2008 | Fleenor et al. |
| 8,876,812 B2 | 11/2014 | Aramayo |
| 2001/0029367 A1* | 10/2001 | Fleenor ............... A61B 18/16 606/32 |
| 2003/0189037 A1 | 10/2003 | Kochman et al. |
| 2004/0116919 A1* | 6/2004 | Heim .................. A61B 18/12 606/34 |
| 2005/0101947 A1 | 5/2005 | Jarrard et al. |
| 2005/0113817 A1 | 5/2005 | Isaacson |
| 2006/0074411 A1* | 4/2006 | Carmel ............... A61B 18/16 606/32 |
| 2008/0249521 A1* | 10/2008 | Dunning ............. A61B 18/16 606/35 |
| 2008/0249524 A1 | 10/2008 | Dunning |
| 2009/0149852 A1 | 6/2009 | Eggers |
| 2009/0171341 A1 | 7/2009 | Karl et al. |
| 2009/0209953 A1 | 8/2009 | Schoenman |
| 2010/0217260 A1 | 8/2010 | Aramayo |
| 2015/0182278 A1 | 7/2015 | Ehninger |

FOREIGN PATENT DOCUMENTS

| | | |
|---|---|---|
| JP | S55-168317 | 12/1980 |
| JP | S57-154409 | 9/1982 |
| JP | S57188250 | 11/1982 |
| JP | S63-54148 | 3/1998 |
| TW | 200633334 | 9/2006 |
| TW | M442080 | 12/2012 |
| WO | WO 2008/013459 | 1/2008 |

OTHER PUBLICATIONS

Notice of Allowance for U.S. Appl. No. 12/703,475 dated Jul. 11, 2014.
International Search Report and Opinion, PCT/US2010/024615.
Wald, et al., "Accidental Burns Associated With Electrocautery," JAMA, Aug. 16, 1971, vol. 217, No. 7, pp. 916-921.
Non-Final Office Action, U.S. Appl. No. 12/703,475, dated Aug. 30, 2013.
Final Office Action, U.S. Appl. No. 12/703,475, dated Apr. 16, 2013.
Non-Final Office Action, U.S. Appl. No. 12/703,475, dated Nov. 23, 2012.
Supplementary European Search Report for application EP 14874779 dated Jul. 17, 2017.

* cited by examiner

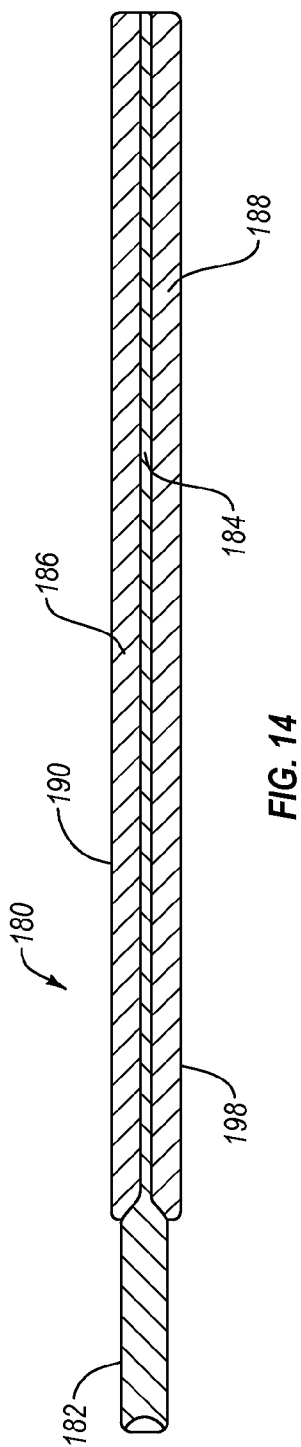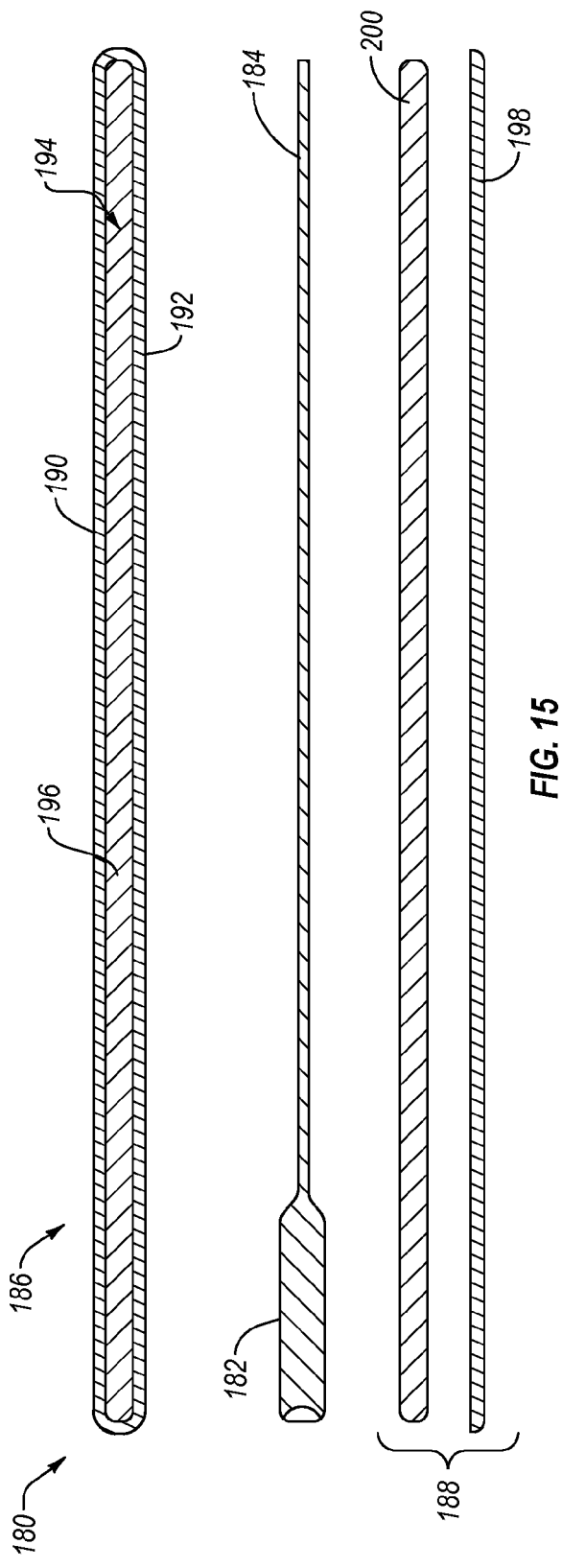
FIG. 14
FIG. 15

UNIVERSAL SELF-LIMITING ELECTROSURGICAL RETURN ELECTRODE

BACKGROUND

1. Technical Field

The present disclosure relates generally to electrosurgical systems. In particular, the present disclosure relates to universal safety electrosurgical return electrodes that are adapted to be used with patients of substantially any size.

2. The Relevant Technology

In the area of electrosurgery, medical procedures of cutting tissue and/or cauterizing leaking blood vessels are performed by utilizing radio frequency (RF) electrical energy. As is known to those skilled in the medical arts, electrosurgery is widely used and offers many advantages including that of the use of a single surgical tool for both cutting and coagulation. The RF energy is produced by a wave generator and transmitted to a patient's tissue through a hand-held electrode that is operated by a surgeon.

Every monopolar electrosurgical generator system must have an active electrode that is applied by the surgeon to the patient at the surgical site to perform surgery and a return path from the patient back to the generator. The active electrode at the point of contact with the patient must be small in size to produce a high current density in order to produce a surgical effect of cutting or coagulating tissue. The return electrode, which carries the same current as the active electrode, must be large enough in effective surface area at the point of communication with the patient such that a low density current flows from the patient to the return electrode. If a relatively high current density is produced at the return electrode, the temperature of the patient's skin and tissue will rise in this area and can result in an undesirable patient burn. According to the Emergency Care Research Institute, a well-known medical testing agency, the heating of body tissue to the threshold of necrosis occurs when the current density exceeds 100 milliamperes per square centimeter. Furthermore, the International Electrotechnical Commission ("IEC") has published standards that require that the maximum patient surface tissue temperature adjacent an electrosurgical return electrode shall not rise more than six degrees) (6° Celsius under stated test conditions.

Since the inception of electrosurgery, various types of return electrodes have been used. Initially, return electrodes consisted of flat stainless steel plates (which in later years were coated with a conductive gel) that were placed under the patient's buttocks, thigh, shoulders, or any location where gravity could ensure adequate contact area. Due to adjustments during a procedure, however, the contact area between the patient and the steel plate sometimes dropped below adequate levels. In such instances, the density of the current being transferred from the patient to the steel plate sometimes increased to levels that resulted in the patients being burned.

In an effort to improve the safety of return electrodes, the flat steel plates were eventually replaced with flexible return electrodes. Like the steel plate electrodes, the flexible return electrodes are also coated with a conductive or dielectric polymer. Additionally, the flexible return electrodes have an adhesive border on them so they can be attached to the patient without the aid of gravity. Because these flexible return electrodes are attached to the patients with an adhesive, these types of return electrodes are often referred to as "sticky pads." Upon completion of the electrosurgical procedure, these sticky pads are disposed of. Expectedly, the disposable nature of sticky pads has resulted in additional surgical costs in the United States of several tens of millions of dollars each year.

The use of sticky pads has resulted in fewer patient return electrode burns compared to the old steel plates. Nevertheless, hospitals are still experiencing some patient burns caused by sticky pads that accidentally fall off or partially separate from the patient during surgery. Furthermore, in order to achieve the reduced number of patient burns, the size and shape of the sticky pads have to match the available surface area of the patient.

For instance, if an adult sized sticky pad were used on a baby, parts of the sticky pad would not be in contact with the baby. As a result, the current density through the portion of the sticky pad that is in contact with the baby may increase to levels that cause burns on the baby. Additionally, the unattached portions of the sticky pad could also pose a burn risk to operating room personnel.

Additionally, due to the smaller surface areas of the sticky pads, the power settings on the generators must be limited to control/limit the current density being transferred through the sticky pads. As a result, for instance, an infant sized sticky pad cannot be used on an adult patient because the required power settings to achieve the desired surgical effect cannot be used without the risk of causing a sticky pad site burn due to the small surface area.

In further attempts to alleviate the foregoing issues, standards (IEC 60601-2-25$^{th}$ Edition) have been established that divide patients in three weight ranges: less than 5 kg, 5 kg to 15 kg, and over 15 kg. Sticky pads have been made specifically sized to accommodate each weight range. Additionally, power setting limits have been established for sticky pads used in each weight range. Specifically, the IEC standards require that the electrosurgical current used with the sticky pads for the less than 5 kg weight category not exceed 350 milliamperes ("mA"). Similarly, the IEC standards require that the electrosurgical current used with the sticky pads for the 5 kg to 15 kg and the over 15 kg weight categories not exceed 500 mA and 700 mA, respectively.

Subsequently, there was proposed a further improvement, an Electrode Contact Quality Monitoring System that would monitor the contact area of the electrode that is in contact with the patient and turn off the electrosurgical generator whenever there was insufficient contact area. Such circuits are shown, for example, in U.S. Pat. No. 4,231,372, issued to Newton, and entitled "Safety Monitoring Circuit for Electrosurgical Unit," the disclosure of which is incorporated by this reference. This system has resulted in additional reduction in patient return electrode burns, but requires a special disposable electrode and an added circuit in the generator that drives the cost per procedure even higher. Additionally, these types of monitoring systems only provide a relative amount of safety. More specifically, such monitoring systems are controlled by human generated algorithms. In creating such algorithms, the algorithm creator must decide what parameters (e.g., contact area size, etc.) are considered safe. In use, however, the selected parameters may prove not to provide sufficient safety. Thus, the safety of such monitoring systems is only as good as the parameters selected for the algorithm in the monitoring system. In the first twenty years after this system was introduced, fewer than 40 percent of all the surgical operations performed in the United States used this system because of its high costs.

One of the biggest improvements to electrosurgery came in the form of self-limiting return electrodes. Unlike sticky pads and steel plate return electrodes, self-limiting return electrodes are relatively large, thereby eliminating the need for conductive gels that may irritate a patient's skin. Additionally, self-limiting return electrodes typically employ geometries and materials whose impedance characteristics, at typically used electrosurgical frequencies, are such that the return electrode self-limits current densities (and corresponding temperature rises) to safe thresholds, should the contact area between the patient and the electrode be reduced below otherwise desirable levels. Furthermore, self-limiting return electrodes were specifically designed to evenly distribute the current density over the entire contact area between the patient and the return electrode. The even distribution of the current density was intended to further reduce the risk of patient burns.

While the use of self-limiting return electrodes has even more dramatically reduced the number of patient burns experienced during electrosurgical procedures, typical self-limiting return electrodes still suffer from some limitations. For instance, like sticky pads, typical self-limiting return electrodes are commonly made in multiple sizes for different sized patients. For instance, a typical self-limiting return electrode for a relatively small person (e.g., under 50 lbs) may be about 26×12 inches while a typical self-limiting return electrode for a larger person may be about 46×20 inches.

Furthermore, typical self-limiting return electrodes are often asymmetrical in their construction such that only one surface of the electrode can be used as a working surface. As a result, operating room personnel must take care to ensure that the return electrode is positioned on the operating room table with the proper surface facing upward toward the patient. If the working surface is not positioned towards the patient, there may be insufficient capacitive coupling between the patient and the return electrode for the return electrode to function properly.

The asymmetrical nature of the construction is often due to the inclusion of additional or thicker layers of materials (e.g., dielectric, cushioning, etc.) on one side of a conductive element than on another side. Not only does the asymmetrical construction of typical self-limiting return electrodes limit which surfaces can be used as working surfaces, but the thickness of some of the layers can limit the ability of the return electrode to work across different categories of patients. For instance, a self-limiting return electrode that works for an adult may not provide sufficient coupling for an infant because a cushion layer is too thick.

Thus, although various advances have been made in the electrosurgical arts, there remains room for improvement. More particularly, while systems and devices have been developed to increase the safety of patients undergoing electrosurgical procedures, such as by reducing the number of patient return electrode burns, the versatility of return electrodes has remained an issue. In particular, as noted above, previous return electrodes have needed to be tailored to different categories of patients (typically size categories) and have been limited in the particular manner of use (e.g., current levels, orientation of working surface, etc.).

Therefore, it would be an advance in the present electrosurgical art to provide a universal safety electrosurgical return electrode that is self-limiting and that can be used across all categories of patients and in more versatile ways.

BRIEF SUMMARY

The present disclosure addresses the foregoing shortcomings by providing a self-limiting return electrode that can be used with essentially any patient, regardless of size or weight, and that is more symmetrical such that multiple surfaces of the return electrode function as working surfaces.

Briefly, return electrodes according to the disclosed embodiments include a relatively large effective surface area compared to sticky pads and steel plate return electrodes. It is so large and so adapted for positioning relative to the body of a patient that it eliminates the need for conductive gels. Moreover, the exposed surface is of a material that is readily washable, disenfectable, and/or sterilizable so as to facilitate easy and rapid conditioning for repeated use. It employs geometries and materials whose impedance characteristics, at typically used electrosurgical frequencies, are such that it self-limits current densities (and corresponding temperature rises) to safe thresholds, should the effective area of the working surfaces of the electrode be reduced below otherwise desirable levels. Accordingly, the need for the foregoing expensive and only relatively safe monitoring circuits in specialized RF generators is eliminated.

In accordance with some embodiments, an electrosurgical return electrode is made sufficiently large to present sufficiently low electrical impedance and low current densities at typical electrosurgical frequencies used in medical procedures to reduce the possibility of excessive temperature elevation in adjacent patient tissue, (i.e., by maintaining temperature ("T") rise below six degrees (6°) Celsius) thereby avoiding tissue necrosis or other undesired patient trauma.

In accordance with some embodiments, the return electrode can have a substantially symmetrical construction such that opposing major surfaces of the return electrode can each function as a working surface (the surface of the return electrode that is in contact with or in close proximity to the patient during a procedure). Furthermore, each working surface of the return electrode is made sufficiently large in area so that in normal use, current flow will not be reduced to a point where it impedes the surgeon's ability to perform surgery at the surgical site.

In accordance with embodiments of the present invention, the return electrode can be used across wide categories of patients. For instance, a return electrode according to some embodiments can be used on patients of substantially any weight. Similarly, a return electrode according to some embodiments can be used on patients that weight 0.8 lb or more. According to still other embodiments, a return electrode can be used on patients from multiple weight categories as defined by industry standards (e.g., IEC). For instance, a single return electrode can be used on any patient regardless of whether that patient falls within the less than 5 kg category, the 5 kg to 15 kg category, or the above 15 kg category.

In accordance with some embodiments, a universal safety return electrode self-limits current densities (and corresponding temperature rises) to safe thresholds while the current density across the contact area between the patient and the return electrode are non-uniform. The non-uniform current density distribution can enable the return electrode to be used with patients of substantially any size while still providing the self-limiting features discussed herein.

In accordance with some embodiments, controlled electrical conductivity is imparted to the electrode by the inclusion therein of electrically conductive materials such as conductive threads or carbon black, thus conditioning conductivity as a function of surface area to levels which limit passage of current therethrough to safe values.

In accordance with some embodiments, the electrical impedance of the materials in and adjacent to the working surface of the electrode is sufficiently elevated so as to limit current density at the working surfaces to a level below the threshold of patient tissue trauma, thus providing a self-limiting characteristic to prevent patient trauma in the event of accidental reduction of the effective working surface of the electrode.

Additional features and advantages of the disclosed embodiments will be set forth in the description which follows, and in part will be obvious from the description, or may be learned by the practice of the invention. These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 14 is a simplified cross section taken along the lines 14-14 of FIG. 13;

FIG. 15 is a simplified exploded cross section of the electrosurgical return electrode of FIG. 13.

DETAILED DESCRIPTION OF THE PREFERRED EMBODIMENTS

The electrosurgical return electrodes disclosed herein employ geometries and materials whose impedance characteristics, at typically used electrosurgical frequencies, are such that they self-limit current densities (and corresponding temperature rises) to safe thresholds, should the contact area between a patient and an effective working surface of the electrode be reduced below otherwise desirable levels. Additionally, the disclosed self-limiting electrosurgical electrodes are capable of being used with patients of substantially any weight or size. Accordingly, the return electrodes disclosed herein may be referred to as "universal safety return electrodes" or "universal self-limiting return electrodes." Furthermore, some of the disclosed self-limiting electrosurgical electrodes have a substantially symmetrical construction such that the electrodes have two major surfaces that can be used as effective working surfaces.

FIGS. 1-12 and the corresponding discussion relate to the structures and features of universal safety electrosurgical electrodes that provide self-limiting characteristics and that can be used with patients of substantially any size based on the assumption that patients are purely conductive. Included in such discussion is a detailed description of an illustrative embodiment of a universal self-limiting return electrode that can be used with substantially any sized patient.

Similarly, FIGS. 13-16 and the corresponding discussion relate to the structures and features of universal safety electrosurgical electrodes that provide self-limiting characteristics and that can be used with patients of substantially any size. Unlike the embodiments and discussion provided in connection with FIGS. 1-12, the embodiments and discussion provided in connection with FIGS. 13-16 are based on the assumption that patients are both conductive and resistive (e.g., some tissue is conductive and some tissue is resistive), not purely conductive. Included in such discussion is a detailed description of an illustrative embodiment of a universal self-limiting return electrode that can be used with substantially any sized patient.

Figure 1:
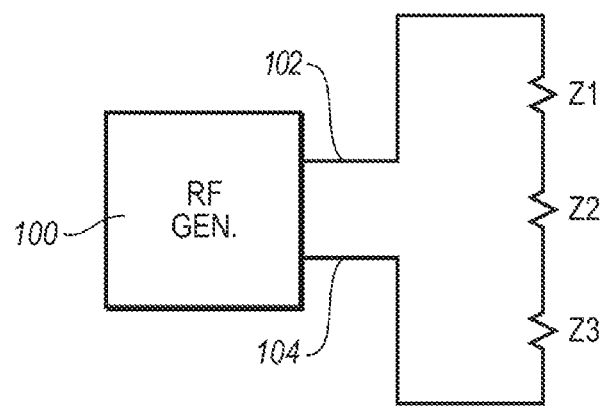
FIG. 1 is a simplified electrical schematic diagram illustrating typical impedances effectively included in the operative path of radio frequency current flow as presented to an electrosurgical generator during an operative procedure.

Now turning to the drawings, and more particularly FIG. 1 thereof, it will be seen to depict a simplified electrical schematic diagram illustrating typical impedances effectively included in the operative path of radio frequency current flow as presented to an electrosurgical generator during an operative procedure. There, it will be seen are conventional radio frequency electrical power generator 100, such as but not limited to constant power, voltage, and/or current or variable power, voltage, and/or current generators. Connected to electrical power generator 100 are conventional electrical conductors 102 and 104 which respectively connect generator 100 to the surgeon's implement represented by impedance $z_1$ and an electrosurgical return electrode represented by impedance $z_3$. Impedance $z_2$ is provided to represent the impedance presented by the patient's tissue lying between the operation site and the return electrode. Electrical conductors 102 and 104 are representative of one illustrative structure that is capable of performing the function of connecting means for making electrical connection to the return electrode. It may be appreciated by one skilled in the art, however, that various other structures are appropriate and capable of performing the desired function.

Although the diagram of FIG. 1 is simplified and generally considers circuit elements in terms of the principal resistances, including the reactants contributed by the surgical instrument, the patient's body and the return electrode, so as to clearly and succinctly illustrate principles of the invention, it should be understood that in reality certain other parameters would be encountered, parameters such as distributed inductance and distributed capacitance which, for purposes of clarity in illustration of the principles hereof, are deemed relatively small and so not considered at this point in this description. However, as set forth below, in one embodiment when an insulating sleeve is interposed between the electrode and the body of a patient, a significant element of capacitive reactance may be included in the impedance of $Z_3$. It should also be noted that FIGS. 1-5 are intentionally simplified so as to present the principles of the invention succinctly. The discussion of FIGS. 6-12 includes a more detailed and complete description of the self-limiting features according to some of the embodiments disclosed herein, including the theoretical basis and exemplary geometries and materials used to achieve the self-limiting features.

The initial embodiment, hereof, is that of an electrode operating in a combined resistive and/or capacitive mode. Accordingly, if the relatively small stray capacitive and inductive reactants are disregarded, the total effective impedance of the circuit will be equal to the sum of the individual impedances $z_1$, $z_2$ and $z_3$; and since essentially the same current will pass through all three, the voltage generated by RF generator 100 will be distributed across impedances $z_1$, $z_2$, and $z_3$ in direct proportion to their respective values. Thus, the surgical energy stored in each of such components will also be directly proportional to their values.

Since it is desired that developed energy be concentrated in the region where the surgeon's implement contacts the patient's tissue, it is desirable that the resistive component of the impedance represented by $z_1$ be substantial and that current passing therethrough be concentrated in a very small region. The latter is accomplished by making the region of contact with the patient at the operative site very small.

It is known that, in contrast with the foregoing series circuit, components of combined resistive and capacitive reactance, when connected in parallel, present a total effective impedance that is given by the formula:

$$z_{\textit{eff}} = \frac{1}{\frac{1}{z_1} + \frac{1}{z_2} + \frac{1}{z_3} + \frac{1}{z_4} + \frac{1}{z_5} + \frac{1}{z_6} \cdots} \quad (1)$$

Thus, if 100 similar impedances, each of 100 ohms, were connected in parallel, the effective impedance $Z_{\textit{eff}}$ would equal one ohm. If half of such impedances were effectively disconnected, the remaining effective impedance would be two ohms, and if only one of the impedances were active in the circuit, the remaining effective impedance would be 100 ohms. The significance of these considerations and their employment to render the electrode hereof self-limiting and fail-safe will be evident from the following description of the elements illustrated in FIGS. 2A, 2B, 2C, and 3.

Figure 2A:
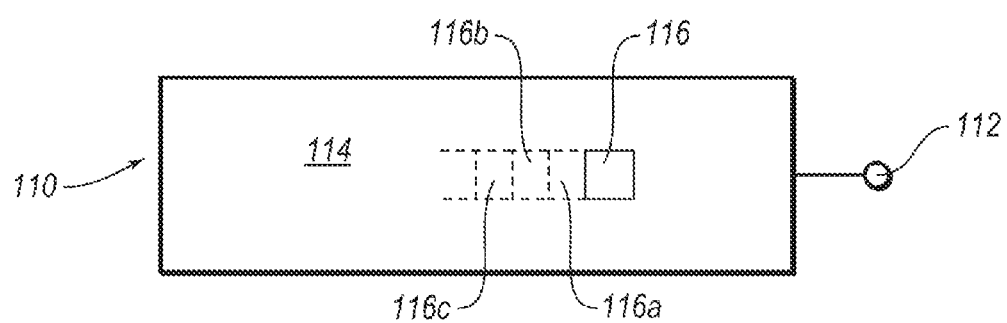
FIG. 2A is a top view of a wide-area distributed electrosurgical return electrode illustrating the principles of the invention.

Now turning to FIG. 2A, there will be seen a schematic representation of the top view of a wide-area distributed electrosurgical return electrode 110 illustrating the principles of the invention. At the right hand side of the figure there is shown an electrical connection terminal 112 to facilitate connection to an electrical return conductor, such as conductor 104 of FIG. 1.

The surface 114 of return electrode 110 is preferably smooth and homogeneous and includes a thin resistive and/or dielectric layer. Alternatively, surface 114 of return electrode 110 may include a capacitive and/or inductive layer, depending on the particular operation of return electrode 110. For instructional purposes of this description and to aid in the mathematical modeling of return electrode 110, electrode 110 may be thought of as including a plurality of uniformly-sized regions or segments as represented by regions 116, 116a, 116b, 116c . . . 116n. It will be appreciated by one skilled in the art, however, that return electrode 110 may or may not include discontinuous regions or segment, it being preferred that electrode 110 have continuous segments.

Figure 2B:
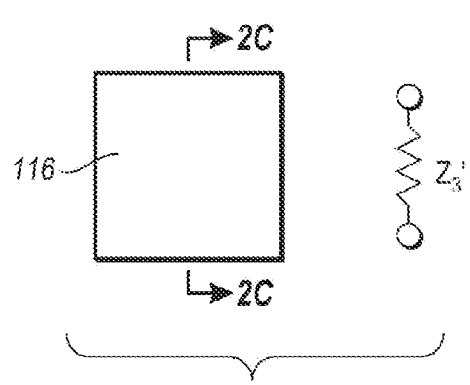
FIG. 2B is an enlargement of a segment of the electrosurgical return electrode of FIG. 2A.

Region/segment 116 is shown larger in FIG. 2B in order to be similar in scale to the resistive impedance $z_3'$ it represents. It thus will now be evident that each of the segments of electrode 110 corresponding to segments 116 . . . 116n inherently has the capability of presenting an impedance similar to that of impedance $z_3'$. However, the number of such segments which are effectively active in parallel within the circuit is a direct function of the surface area of the patient that overlies the electrode. Thus, in the case of a large supine patient whose body is in effective contact with 50 percent (50%) of the upper surface of the electrode, 50 percent of the segments corresponding to segments 116-116n will be effectively paralleled in the circuit to form an impedance represented by impedance $z_3$ of FIG. 1; and, accordingly, if electrode 110 contains 100 segments of 100 ohms each, the effective impedance operatively presented by the effective 50 percent of the electrode elements would be 2 ohms. Since 2 ohms is very small compared with the impedance represented by elements $z_1$ and $z_2$, very little surgical energy is available at the surgical site, and due also to the relatively large effective working area of the electrode, current density and temperature elevation are maintained below the danger thresholds mentioned above.

Now, if for any reason, the effective contact area between the patient and electrode were to be reduced to the surface of only one of the segments 116-116n, then the effective impedance (combined capacitive reactance and resistance in the example under consideration) would increase to 100 ohms; and at some point of reduction in contact area, the effective impedance would rise to a level relative to the impedance presented at the site of the electrosurgical instrument so as to diminish the electrosurgical effect of the surgical instrument or otherwise prevent effective use of the instrument by the surgeon, thus signaling the surgeon that the patient should be repositioned so as to present a greater surface area in contact with the return electrode. At the same time, the total circuit impedance would be increased so that the total current that would flow if the surgeon attempted to employ his instrument without repositioning the patient would be reduced to a value below that which would cause undesired trauma to the patient. Accordingly, there is provided a self-limiting feature that enhances safety in use (through the natural characteristics of the return electrode) without the need for the aforementioned separate circuit monitoring and control circuits, with their human generated algorithms that only provide a relative level of safety.

Figure 2C:
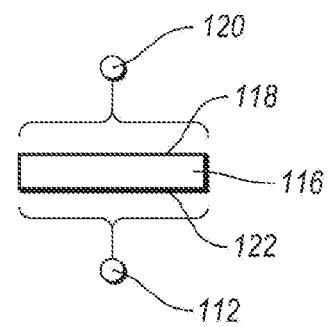
FIG. 2C is a cross section taken along the section lines 2C-2C of FIG. 2B and illustrating the effective circuit impedance represented by the segment of 2B.

FIG. 2C is a cross section taken along the section lines 2C-2C of FIG. 2B and illustrates the effective circuit impedance $z_3$ represented by the segment 116 of 2B. There, in FIG. 2C are seen small segment 116 with its upper patient-contacting surface 118 represented electrically by terminal 120 and its lower surface 122 represented by electrical terminal 112. For the purpose of this description (and in order to present the principles underlying this embodiment clearly), the impedance $z_3$ may be thought of as existing between terminals 120 and 112. Of course, it will be evident to those skilled in the art that in an embodiment in which a thin but highly conductive layer is included along the lower surface of electrode 110, each of the impedances represented by the remaining segments are connected at their lower extremities in parallel to terminal 112; whereas, if such highly conductive layer is absent, then, in addition to the impedance represented by the material lying between the upper and lower regions of each segment, there will be an additional impedance (not shown) that is represented by the material through which current would have to pass transversely or laterally through the electrode in order to get to terminal 112.

It should now be evident that if lateral impedance is minimized by provision of the aforementioned thin conducting layer, or if the effective conductivity at the lower part of the material of region 116 is otherwise increased, the effective impedance presented by the return electrode will be inversely proportional to the effective upper surface of the electrode that is in contact with a patient.

Figure 3:
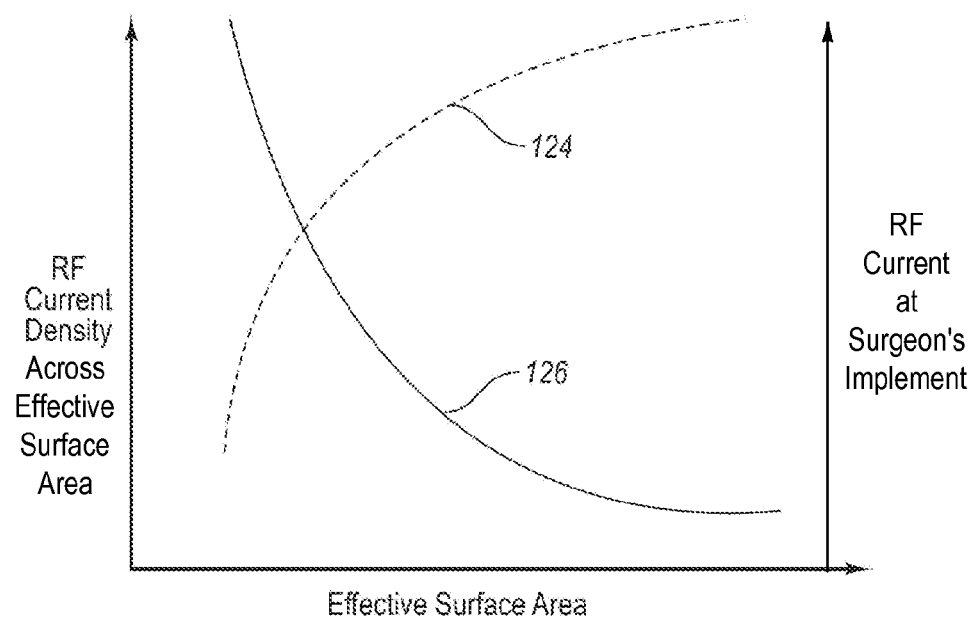
FIG. 3 is a chart illustrating in graphical form the relationships between effective surface area of the return electrode and the effective radio frequency current density developed at the electrode.

FIG. 3 is a chart generally illustrating in graphic form the relationships between the effective surface area of the return electrode and (i) the effective radio frequency current densities developed at the electrode and (ii) the radio frequency current available at the surgeon's implement. However, before proceeding to a consideration of such chart, it should be noted that the chart is simplified so as to illustrate the principles underlying the invention and does not represent actual data that may vary substantially. For instance, it will be understood that the scale of the current density across the effective surface area shown on the y-axis on the left side of the chart will be different (and the value will be much lower) than the scale of the current available at the surgeon's implement shown on the y-axis on the right side of the chart.

In FIG. 3 there is seen a plot of RF Current Density versus Electrode Effective Surface Area, the latter (as should now be evident to those skilled in the art) being that part of the surface of the return electrode that makes effective electrical contact with the body of a patient. As would be expected from the foregoing discussion, when the effective area is large, the current at the surgeon's implement is high (dashed graph line 124) and the corresponding current density across the return electrode is very low (solid graph line 126). This is, of course, the condition desired for conducting electrosurgery. However, if we assume constant current throughout the circuit, as the effective surface area decreases, the current density across the return electrode (solid graph line 126) increases with a corresponding decrease in the current at the surgeon's instrument (dashed graph line 124). When the effective surface area declines to some predetermined point, there will remain insufficient current at the surgical instrument to effectively conduct electrosurgery.

It may be appreciated by one skilled in the art that the change in current density and available current to the surgeon may or may not occur simultaneously with the variations in effective surface area. Various embodiments of the present invention may have substantially simultaneous changes in current density and available current, while other embodiments of the present invention may include a lag period therebetween.

The parameters selected for the materials and electrode dimensions are chosen so that current density and corresponding tissue temperature elevation adjacent the return electrode do not exceed the limits mentioned in the introduction hereof. It will now be seen that by a proper selection of such parameters the return electrode is made self-limiting, thereby obviating the need for the additional monitoring circuits to which reference is made above.

To facilitate description of the principles underlying the invention, the foregoing is described in terms of impedances whose principal components are resistances and capacitive reactants. However, the principles of the invention are also applicable to other embodiments in which the impedances include any combination of resistive, capacitive and/or inductive impedances.

The invention hereof is now further described in connection with applications in which an effective dielectric layer is represented by, for example: (i) a physical dielectric layer on the upper surface of the electrode; (ii) the material of a surgical gown worn by the patient; (iii) a bed sheet or other operating room linens interposed between the patient and the return electrode; (iv) the material of a protective sleeve fitted over the return electrode; (v) or any combination thereof.

Figure 4:
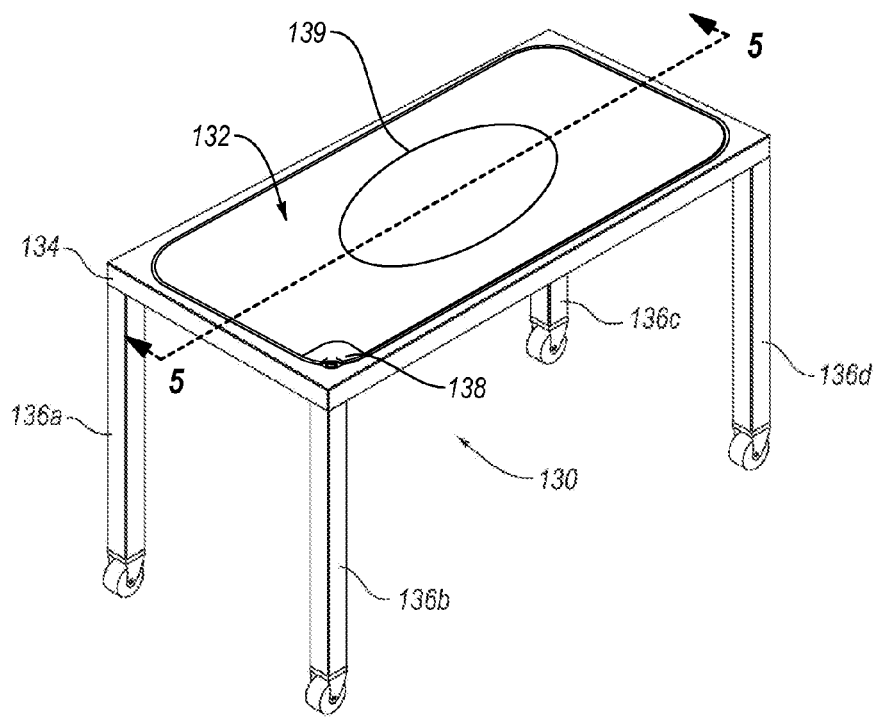
FIG. 4 is a perspective view showing an operating table with an electrosurgical return electrode according to the present disclosure disposed on the upper surface thereof.
Figure 5:
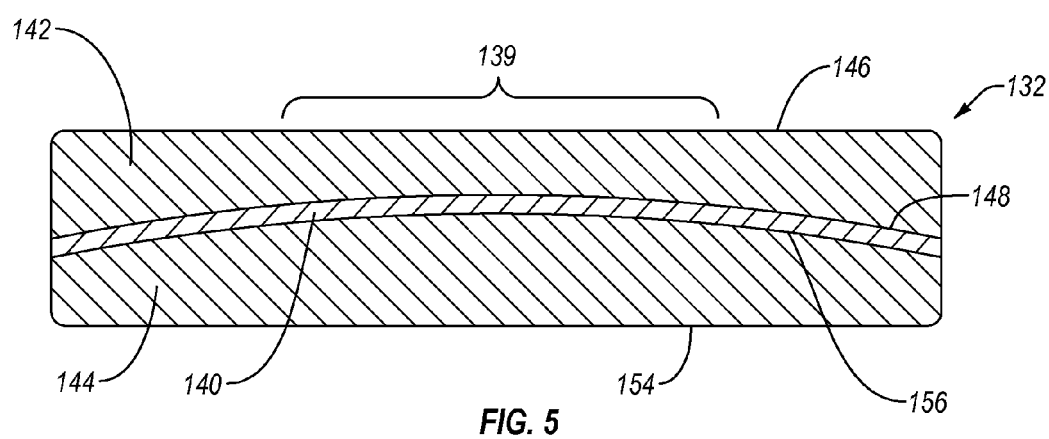
FIG. 5 is a simplified cross section taken along the lines 5-5 of FIG. 4.

Reference is now made to FIGS. 4-5, which illustrate an electrosurgical return electrode 132 according to the present disclosure. In FIG. 4, electrosurgical return electrode 132 is shown in perspective an operating table 130 with electrosurgical return electrode 132 according to the present disclosure disposed on the upper surface thereof, an edge of table 130 being identified by reference number 134. Operating table 130 is shown to have conventional legs 136a-136d that may be fitted with wheels or rollers as shown. Table 130 is one structure that is capable of performing the function of supporting means for supporting a patient during treatment. It may be appreciated by one skilled in the art, however, that various other configurations of support means are possible and capable of performing the required function. For example, supporting means may include but not be limited to chairs, plates, beds, carts, and the like.

Although, in FIG. 4, the entire upper surface of table 130 is shown as being covered with return electrode 132, it should be understood that entire coverage is by no means required in order to practice the principles of the invention. Thus, when used with conventional electrosurgical generators, the return electrode needs only to present an effective working surface area which is sufficient to provide adequate resistive, capacitive, or inductive coupling at the typically employed RF frequencies so as not to interfere with the surgeon's ability to perform surgery while at the same time avoiding undesired tissue damage. It has been found that at conventional electrosurgical frequencies, this has necessitated only an effective working surface area no larger than about the projected outline of one-third of the torso for an adult patient lying on an operating table or a portion of the buttocks of a patient sitting in a chair. However, the effective working surface area will vary depending on the material used, in some geometrical configurations, and in instances where various layers of operating room linens are placed over the electrode. The principles hereof may be successfully employed and the effective working surface area of the return electrode determined in such circumstances by routine experimentation. Under certain conditions, the effective working surface may be as small as about seven square inches (or about 45 square centimeters).

Moreover, although return electrode 132 shown in FIGS. 4-5 is depicted as being rectangular in shape, it will be evident that return electrodes according to the present disclosure could be oval or contoured as, for example, to follow the silhouette of the at least a portion of the torso or other principal part of the body of a patient. As will be evident from the foregoing, it is important that the electrode be configured so that when the electrode is used: (1) the return current density on the surface of the patient is sufficiently low; (2) the electrical impedance between the electrode and the patient is sufficiently low so that electrical energy is not concentrated sufficiently to heat the skin of the patient at any location in the electrical return path by more than six degrees (6°) Celsius; and (3) the characteristics of the materials and geometries are such that if the effective area of the electrode is reduced below a selected threshold level, there will be insufficient energy dissipated at the surgeon's implement for him to continue effectively using the implement in its electrosurgical mode.

As will be recognized by those skilled in the art, it is not necessary for there to be direct ohmic contact between the skin of a patient and the return electrode hereof for the electrode to perform generally according the foregoing description, for although capacitive reactance (represented by the distance between a patient's body and the electrode) will be introduced if something such as a surgical gown separates them, such capacitive reactance will modify rather than destroy the impedance identified as $z_3$.

As is known to those skilled in the art, in an alternating current circuit (e.g., such as those used in electrosurgery) the capacitive reactance of an impedance is a function both of capacitance and the frequency of the alternating current electrical signal presented to the reactance. Thus, the formula for capacitive reactance (in ohms) is:

$$Xc = \frac{1}{2\pi f C} \quad (2)$$

where Xc is capacitive reactance in ohms, π is 3.14159, f is frequency in hertz, and C is capacitance in farads.

The formula for capacitance in a parallel plate capacitor is:

$$C = \frac{\kappa \varepsilon_0 A}{t} \quad (3)$$

where C is capacitance in Farads, κ is the dielectric constant of the material lying between the effective plates of the capacitor, A is the area of the smallest one of the effective plates of the capacitor in square meters, t is the separation of the surfaces of the effective plates in meters, and $\varepsilon_0$ is the permittivity of air in Farads/meter. Thus, it will be seen that to meet maximum permissible temperature rise criteria in an embodiment in which electrode circuit capacitance is substantial, different minimum sizes of electrodes may be required depending upon the frequency of the electrical generator source, the separation of the body of the patient from the electrode, and the material lying between the effective conductive region of the electrode and the adjacent body surface. Accordingly, although the principles of the disclosure are applicable to a wide range of frequencies of electrosurgical energy, the considerations set forth herein for minimum sizes of return electrodes specifically contemplate frequencies typically employed in conventional electrosurgical energy generators.

Those skilled in the art know that, with the currently used disposable return electrodes, reducing the effective size of the electrode to about three square inches will not reduce the RF current flow to a level where it will impede the surgeon's ability to perform surgery nor concentrate current to a level to cause patient trauma. However, to provide for some spacing of the electrode from patient's body, a return electrode according to the present disclosure, would need a minimum effective area of between about 7 and about 11 square inches (about 45 cm² to about 70 cm²) with a relatively small separation from the skin of the patient such as that provided by a surgical gown or no interposing gown at all. Such an effective area is easy to obtain if the patient is positioned on an electrode that is the size of at least a portion of their upper torso or larger.

The characteristics of the desired dielectric for the present embodiment are sufficiently comparable to those of selected rubbers, plastics and other related materials that the latter may be satisfactorily employed as materials for the return electrode. As mentioned above, with such a return electrode, if the patient is positioned such that not enough of the return electrode is in close proximity to the patient to result in as low impedance as needed, the results would be that the current flow from the electrosurgical generator would be reduced to a level making it difficult for the surgeon to perform surgery. Thus, in the present embodiment, notwithstanding interposition of some additional capacitance represented by a surgical gown, the features described above will continue to occur.

It will be observed that when return electrode 132 is laid out on operating table 130, the upper exposed, or working, surface of the electrode again is expansive so as to meet the foregoing criteria for low impedance. Although it is not necessary that the electrode cover the entire surface of an operating table or the entire seat surface of a dental or other patient chair, it has been found advantageous in some instances to provide a greater surface area than that of the projected area of a portion of the buttocks or torso of a patient so that if a patient moves position during the course of a procedure, a sufficient portion of the patient will remain in registration with the electrode surface so that the effective impedance will remain less than the above-described level.

At this juncture, it may be helpful to emphasize characteristics of the improved electrode according to the invention hereof that are deemed particularly relevant to an understanding of the inventive character thereof. First, as mentioned above, the electrode does not need to be in direct contact with a patient, either directly or through intervening conductive or nonconductive gel. In addition, because of its expansive size, there is no need for tailoring the electrode to fit physical contours of a patient. While it has been found that with selected materials and geometries, the self-correcting and self-limiting principles hereof could be achieved in an electrode as small as about seven square inches (or about 45 square centimeters) in working surface area, the preferable range of exposed upper working surface area of the electrode lies in the range of from about 11 to 1,500 square inches (or about 70 to 9,680 square centimeters). By making the electrode several times larger (typically, at least an order of magnitude larger) in working surface area than steel plates or sticky pads, the need for direct physical attachment, either directly to the skin of the patient or through gels, is eliminated.

Return electrode 132, as illustrated in FIGS. 4-5, may be made of conductive plastic, rubber, or other flexible material which, when employed in the electrode will result in an effective dc resistance presented by each square centimeter of working surface to be greater than about 8000Ω or alternatively provide a bulk impedance of greater than 4000 Ω·cm. Silicone, butyl rubber, or urethane has been found to be particularly attractive materials as they are flexible, as well as readily washable and sterilizable. Alternatively, the main body of the return electrode may be made of inherently relatively high resistance flexible material altered to provide the requisite conductivity. A preferred example of the latter is that of silicone rubber material in which there are impregnated conductive fibers, such as carbon fiber, or in which there have been distributed quantities of other conductive substances such as carbon black, quantities of gold, silver, nickel, copper, steel, iron, stainless steel, brass, aluminum, or other conductors.

Further reference to FIG. 4 reveals the presence of a conventional electrical connector 138 attached to return electrode 132 to provide a conventional electrical return to the electrosurgical radio frequency energy source (not shown). Connector 138 is another structure capable of performing the function of connecting means for making electrical connection to the return electrode. Connector 138 is only illustrative of one possible structure for performing the desired function; it being appreciated by one skilled in the art that various other structures are capable of performing the required function.

FIG. 4 also illustrates that return electrode 132 includes an area 139. Area 139 of return electrode 132 may be adapted to have smaller patients positioned thereon. For instance, area 139 may be sized to have an infant sized patient positioned thereon. Furthermore, as discussed in greater detail below, return electrode 132, and particularly area 139 thereof, may be configured to provide the self-limiting characteristics discussed herein for infant sized patients positioned on area 139. Furthermore, although not illustrated, return electrode may also include additional areas configured to provide self-limiting characteristics for patients from different industry standard weight categories. By way of non-limiting example, area 139 may be configured to provide self-limiting characteristics for patients under 5 kg, a second area may be configured to provide self-limiting characteristics for patients between 5 kg and 15 kg, and a third area may be configured to provide self-limiting characteristics for patients over 15 kg. In some embodiments the areas for different sized patients may overlap one another, while in other embodiments the areas do not overlap. Furthermore, the areas may be formed concentrically with one another.

Attention is now directed to FIG. 5. FIG. 5 illustrates a simplified section taken along the lines 5-5 of FIG. 4. As illustrated in FIG. 5, return electrode 132 includes a conductive element 140 and pads 142, 144 on opposing sides of conductive element 140. Conductive element 140, in one configuration, is made of a conductive plastic, rubber or other flexible material which, when employed as a conductive element, will result in an effective DC resistance presented by each square centimeter of the working surface of return electrode 132 (the surface that is in contact with or in close proximity to the patient) to be greater than about 8000 ohms or alternatively provide a bulk impedance of greater than 4000 Ω·cm. Various materials may be appropriate to give the required impedance. For example, silicone, butyl rubber, or urethane have been found to be particularly attractive materials for conductive element 140 as they are flexible, as well as readily washable, disinfectable, and sterilizable. Alternatively, in another embodiment, conductive element 140 may be made of an inherently relatively high resistance flexible material altered to provide the requisite conductivity. One example of the latter is that of silicone rubber material in which there are impregnated conductive fibers, such as carbon black, quantities of gold, silver, nickel, copper, steel, iron, stainless steel, brass, aluminum, or other conductors.

In yet another alternate configuration, conductive element 140 may be fabricated from a material that is substantially transparent to one or more wavelengths of electromagnetic radiation, such as but not limited to, microwave radiation, infra-red (IR) radiation, ultraviolet (UV) radiation, X-ray radiation, radio frequency (RF), and the like. This allows conductive element 140 and return electrode 132, when the other components of return electrode 132 are transparent to one or more wavelengths of electromagnetic radiation, to be maintained in place during performance of certain medical procedures using particular wavelengths of electromagnetic radiation.

It may be appreciated by one skilled in the art that conductive element 140 may have various other configurations so long as conductive element 140 is capable of performing the functions of an electrode, i.e., being capable of passing current therethrough. For example, in another embodiment, conductive element 140 includes a thin highly conductive lower stratum that facilitates connection of return electrode 132 to an electrosurgical radio frequency energy source (not shown). In another alternate embodiment, conductive element 140 is configured from multiple layers of conductors. In still yet another embodiment, conductive element 140 includes an outer dielectric layer that substantially surrounds an interior-conducting layer, similar to the electrosurgical electrodes described previously.

Referring again to FIG. 5, disposed on opposing sides of conductive element 140 are pads 142, 144. As can be seen, pad 142 has an outer surface 146 and an inner surface 148. Outer surface 146 is configured to be placed against the surface of a patient (thereby acting as a working surface of return electrode 132), while inner surface 148 is disposed next to conductive element 140. In some embodiments, inner surface 148 is secured to conductive element 140, such as with an adhesive, to prevent air bubbles or separation between pad 142 and conductive element 140. Pad 142 may include outer and inner cover layers that are formed individually and secured together about their edges or are integrally formed. The outer and inner cover layers may define outer and inner surfaces 146, 148. Outer and inner cover layers may be formed of various materials, such as urethane. A fill material, discussed below, may be disposed between the outer and inner cover layers.

Similar to pad 142, pad 144 includes an outer surface 154 and an inner surface 156. Outer surface 154 is configured to be placed on a support surface (e.g., operating table, chair, etc.), while inner surface 156 is disposed next to conductive element 140. Like outer and inner cover layers 146, 148, one or both of outer surface 154 and inner surface 156 may be defined by a cover layer formed of various materials, such as urethane. Like pad 142, inner surface 156 may be secured to conductive element 140, such as with an adhesive, to prevent air bubbles or separation between pad 144 and conductive element 140. In other embodiments, however, the edges of pad 144 may be secured to the edges of pad 142 with conductive element 140 disposed therebetween. Also like pad 142, pad 144 may include a fill material.

Fill materials used in pads 142, 144 may provide return electrode 132 with some pressure reducing characteristics. More specifically, since pads 142, 144 retain a defined volume of fill material, when an individual rests upon return electrode 132, the fill materials distribute the downward force of the patient throughout the fill materials, thereby decreasing the point forces applied to those parts of the patient's anatomy where bony prominences are located. Nevertheless, as discussed elsewhere herein, pads 142, 144 are relatively thin to ensure sufficient coupling between a patient and conductive element 140. Accordingly, in some situations, such as during lengthy surgical procedures, it may be desirable or necessary to use a separate pressure reducing pad in combination with return electrode 132 to prevent the formation of pressure sores on the patient or to increase the patient's comfort level.

Fill materials used in pads 142, 144 may act as dielectric layers to reduce the current that flows through pads 142, 144, respectively. Alternatively, the fill materials may take the form of conducting materials to aid with the transmission of current therethrough. Additionally, the fill materials may provide a thermal mass for the distribution of heat during an electrosurgical procedure. As discussed above, IEC requires that during an electrosurgical procedure the temperature rise of the patient's tissue should remain below six degrees Celsius (6° C.). The thermal mass provided by the fill materials assists with the distribution of heat throughout the patient's body and substantially eliminates, in combination with the self-limiting characteristics of return electrode 132, the potential for hot spots that may burn the patient. Consequently, the substances used for fill materials may perform multiple functions during an electrosurgical procedure.

In general, the fill materials may take the form of one or more solids, liquids, gases, or combinations thereof depending on the pressure reducing, dielectric, and/or conducting properties needed for return electrode 132. For example, in one illustrative embodiment, the fill materials are elastomeric gels having low durometer level, such as sorbethane. In addition to sorbethane, various other elastomeric gels may be used, such as but not limited to those based upon the polymer chemistry of urethanes, silicones, hydrophilic elastomers or hydrogels, vinyls, vinyl alcohols, or other similar materials and technologies. Additionally, the fill materials may take the form of water, saline, water based materials, conductive oils, and the like. Still further, the fill materials may take the form of solid but flexible foam-type materials.

The materials forming return electrode 132, conductive element 140, and pads 142, 144, at least partially control the passage of current from a patient to conductive element 140. As such, in one embodiment, pads 142, 144 are insulative, while in an alternate configuration pads 142, 144 may be conductive and aid in the passage of current from the patient to conductive element 140. So long as the total impedance of return electrode 132 is within the limits defined herein, i.e., each square centimeter of a working surface being greater than 8000 ohms or bulk impedance greater than 4000 $\Omega \cdot m$, the various elements of return electrode 132, i.e., conductive element 140 and pads 142, 144, may provide one or more resistive, inductive, and/or capacitive inductance components to the bulk impedance. In this manner return electrode 132 is self-limiting, while also providing at least some pressure reducing characteristics.

In addition to the materials used to form pads 142, 144, the thickness and arrangement of pads 142, 144 and conductive element 140 can affect the transmission of current from a patient to conductive element 140. By way of non-limiting example, the distance between outer surface 146 of pad 142 and conductive element 140 can affect the capacitive coupling between conductive element 140 and a patient resting upon return electrode 132. Through this capacitive coupling, current used during electrosurgery is passed from the patient to return electrode 132. As will be understood by one of ordinary skill in the art in light of the disclosure herein, the capacitive coupling between the patient and return electrode 132 can be directly related to the self-limiting characteristics of return electrode 132. Thus, by changing the distance between the outer surface 146 and the conductive element 140, the capacitive coupling between the patient and the return electrode 132 can be adjusted.

As illustrated in FIG. 5, to make return electrode 132 safe and self-limiting for patients of substantially any size, the distance between surface 146 and conductive element 140 varies. More specifically, portions of conductive element 140 are disposed closer to outer surface 146 than other portions of conductive element 140. In the illustrated embodiment, for instance, conductive element 140 is arranged in an arch, domed, or other curved shape such that the portion of conductive element 140 within area 139 is positioned closer to outer surface 146 than the rest of conductive element 140. In some embodiments, for instance, at least a portion of conductive element 140 within area 139 is spaced apart from outer surface 146 by a distance of less than about 0.120 inches. In other embodiments, at least a portion of conductive element 140 within area 139 is spaced apart from outer surface 146 by a distance of between about 0.02 inches and about 0.120 inches. The spacing between conductive element 140 and outer surface 146 can be achieved by limiting the thickness of at least a portion of pad 142 within area 139 to the noted dimensions (e.g., less than about 0.120 inches, between about 0.02 inches and about 0.120 inches).

Positioning conductive element 140 closer to outer surface 146 increases the capacitive coupling with a patient (or portion of a patient) positioned on area 139. A smaller patient that has less surface area to contact return electrode 132 needs greater capacitive coupling with conductive element 140 in order to effectively and safely (e.g., in a self-limiting manner) transfer electrosurgical current to return electrode 132. Accordingly, a small patient can be placed on area 139 and the relatively small distance between outer surface 146 and conductive element 140 enables sufficient capacitive coupling between the patient and conductive element 140 to effectively and safely transfer electrosurgical current therebetween. In contrast, a larger patient that can make contact with a larger portion of return electrode 132 does not require the same high level of capacitive coupling with conductive element 140 as a small patient. Accordingly, the portion of conductive element 140 outside of area 139 can be spaced further from outer surface 146 while still providing sufficient capacitive coupling between the patient and conductive element 140. It will be appreciated that larger patients may also be positioned on area 139 alone or in addition to other portions of return electrode 132 and return electrode 132 will enable the effective and safe transfer of electrosurgical current.

In addition or as an alternative to adjusting the distance between the outer surface 146 and the conductive element 140, the dielectric constants of the materials used in pad 142 may be adjusted to achieve the desired level of capacitive coupling and/or resistance presented by return electrode 132. As noted above (see Equation 3), the capacitance between the patient and the conductive element 140 is dependent on the thickness of pad 142 therebetween, the amount of contact area between the patient and return electrode 132, as well as the dielectric constants of the pad materials. Accordingly, the materials used to form pad 142 may be selected, as least in part, based upon the value of their dielectric constants. Similarly, the materials used in pad 142 may be altered (e.g., by levels of doping) to adjust their dielectric constants in order to provide the desired capacitance and/or resistance.

Thus, for instance, rather than or in addition to positioning the conductive element 140 closer to outer surface 146 in area 139 than outside of area 139, pad 142 may include areas that have different dielectric constants. By way of example, the portion of pad 142 that is within area 139 may have a dielectric constant that is different that the portion of pad 142 that is outside of area 139. In some embodiments, the portion of pad 142 within area 139 is formed of a different material that the portion of pad 142 outside of area 139, thereby providing the different dielectric constants for the different areas of pad 142. In other embodiments, pad 142 is made of the same material inside and outside of area 139, but the material within one of the portions is altered (e.g., by doping) to adjust the dielectric constant. As a result, the different areas of pad 142 have different dielectric constants.

As discussed elsewhere herein, previous return electrodes were made for specific categories of patients. The categories were typically defined by patient weight ranges (e.g., less than 5 kg, 5 kg to 15 kg, and over 15 kg). In addition to selecting the proper return electrode based on the patient's weight, operating room personnel also needed to ensure that power settings on the electrosurgical generator were set in accordance with the restrictions associated with the particular return electrode used (e.g., to limit current to: 350 mA for patients under 5 kg; 500 mA for patients between 5 kg and 15 kg; and 700 mA for patients over 15 kg). Selecting the correct return electrode and making sure that the settings of the electrosurgical generator were properly set could be confusing and viewed as trivial matters for operating room personnel, especially those not familiar with the principles of electricity.

In contrast, return electrode 132 functions with patients of substantially any size. For instance, in one implementation, return electrode 132 may be used with patients that weigh 0.8 lb or more. In another implementation, return electrode 132 may be used with patients from multiple industry standard weight categories. For instance, return electrode 132 may be used on any patient regardless of whether that patient falls within IEC's less than 5 kg category, 5 kg to 15 kg category, or above 15 kg category. Furthermore, since return electrode 132 can be used with substantially any sized patient, operating personnel do not have to limit or adjust the generator power settings to accommodate different return electrodes.

In connection with FIGS. 6-12, the principles underlying the self-limiting properties of the return electrodes of the present disclosure will be discussed in greater detail. While the following discussion will be made in relation to the simplified return electrodes illustrated in FIGS. 6 and 10, it will be understood that these principles are equally applicable to the other return electrodes disclosed herein.

Figure 6:
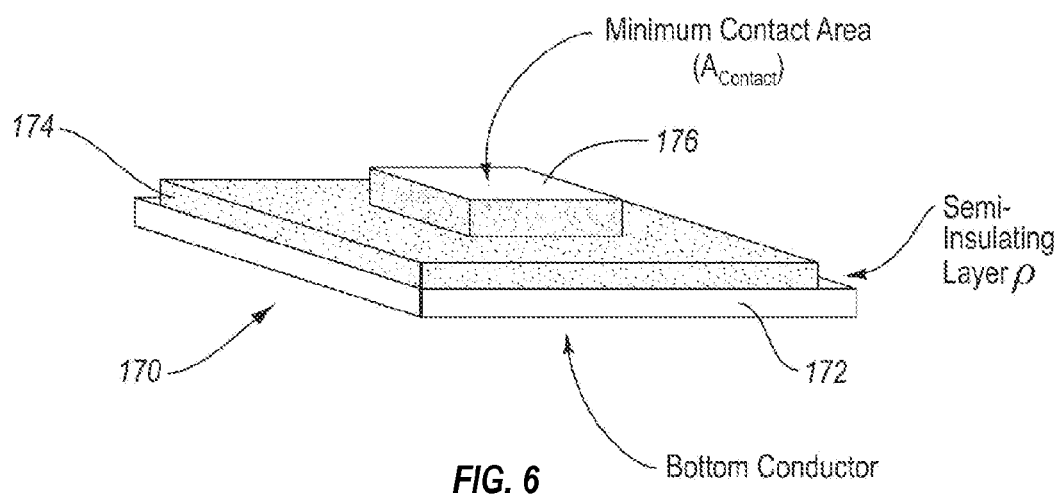
FIG. 6 is a perspective view of an electrode according to the invention illustrating a simulated condition when the effective contact area with a patient is substantially less than the physical electrode size.

FIG. 6 depicts a return electrode 170 consisting of a conductive metal backing 172 and a semi-insulating layer 174. The electrode 170, and more specifically, semi-insulating layer 174, is in contact with another conducting layer 176, which represents a patient thereupon. The self-limiting feature (maintaining current densities below a threshold level) of return electrode 170 arises due to the total impedance of return electrode 170, whether such impedance arises from semi-insulating layer 174 alone or in combination with conductive metal backing 172 and/or conducting layer 176. Furthermore, the total impedance may arise from the various resistive, inductive, and/or capacitive components of conductive metal backing 172, semi-insulating layer 174 and/or conducting layer 176.

Return electrode 170, which includes a single layer of semi-insulating material 174, has a bulk resistivity $\rho$ and thickness t. An area A placed between a conductive surface and the patient may be modeled as a resistor (R) in parallel with a capacitor (C) (See FIG. 11).

For ease of explanation, we will determine the resistive requirements of return electrode 170 for self-limiting in a purely resistive scenario where return electrode 170 is modeled as a resistor in parallel with a capacitor. Following the calculation of the minimum requirements for self-limiting in the purely resistive case, we will generalize the analysis for any impedances, whether such impedances result from resistive, capacitive, and/or inductive components.

As such, the resultant total impedance equivalent for the resistor in parallel with the capacitor combination is:

$$Z_{tot} = R \parallel X_c = \frac{(R)\left(\frac{1}{j\omega C}\right)}{(R) + \left(\frac{1}{j\omega C}\right)} = \frac{R}{1 + j\omega CR} \quad (4)$$

where j is an imaginary component of reactance, and $\omega$ is the angular frequency and is defined as $\omega = 2\pi f$, where f is the electrosurgical generator frequency. The magnitude of the impedance is:

$$|Z_{tot}| = \sqrt{\frac{R^2}{1 + \omega^2 C^2 R^2}} = R\sqrt{\frac{1}{1 + \omega^2 C^2 R^2}} \quad (5)$$

Substituting the dependence of R and C on the area A, thickness t, bulk resistivity $\rho$, and the dielectric constant of the material $\kappa$ defined by:

$$R = \frac{\rho t}{A} \quad (6)$$

and $$C = \frac{\kappa \varepsilon_0 A}{t} \quad (7)$$

where permittivity constant $\varepsilon_0 = 8.85 \times 10^{-12}$ F/m, the magnitude of the total impedance is given by:

$$|Z_{tot}| = \frac{\rho t}{A}\sqrt{\frac{1}{1 + \omega^2\left(\frac{\kappa \varepsilon_0 A}{t}\right)^2\left(\frac{\rho t}{A}\right)^2}} = \frac{\rho t}{A}\sqrt{\frac{1}{1 + \omega^2 \kappa^2 \varepsilon_0^2 \rho^2}} \quad (8)$$

According to the Association for the Advancement of Medical Instrumentation ("AAMI") standard (which has been updated and incorporated into the IEC standards), the total impedance of the electrosurgical electrode should be less than 75Ω under normal operating conditions. It is preferred, therefore, that:

$$\frac{\rho t}{A} \sqrt{\frac{1}{1+\omega^2 \kappa^2 \varepsilon_0^2 \rho^2}} \le 75 \ \Omega \quad (9)$$

We define $\beta$ as $$\beta = \frac{Z_{tot}}{75 \ \Omega} \quad (10)$$

If $\beta \ll 1$, the electrode will have very low impedance compared to the AAMI standard, and the surgeon will not notice any degradation in the electrosurgical cutting power due to the electrode. If $\beta \gg 1$, the electrosurgical electrode will present such a large impedance that the surgeon will no longer be able to perform electrosurgery. Using $\beta$ in the above inequality, the expression becomes the equality:

$$\frac{\rho t}{A} \sqrt{\frac{1}{1+\omega^2 \kappa^2 \varepsilon_0^2 \rho^2}} = 75 \ \beta \quad (11)$$

It is preferred that self-limiting occurs when the electrode has a large electrode area in contact with the patient (see FIG. 10); however it is also necessary for self-limiting to occur when the patient only makes contact with a small fraction of the total electrode area (see FIG. 6). For self-limiting to work properly, it is necessary for the current density (given by I/A), where I is the total current through the contact area A of the electrosurgical return electrode, to not exceed a critical value $$\left(\frac{I}{A}\right) \le \left(\frac{I}{A}\right)_{critical} = 100 \ \text{mA/cm}^2 \quad (12)$$

AAMI standards indicate that normal electrosurgical currents are on the order of 500-700 mA. If we set 1000 mA=$I_{max}$ as a safe upper limit as to what one might expect for an above average power surgery, then, in order to return the current to the electrode without exceeding $I_{critical}$, the contact area $A_{contact(min)}$ for traditional electrosurgical return electrodes must have a minimum size:

$$A_{contact(min)} \ge \frac{I_{max}}{\left(\frac{I}{A}\right)_{critical}} = \frac{1000 \ \text{mA}}{100 \ \text{mA/cm}^2} = 10 \ \text{cm}^2 \quad (13)$$

It can be appreciated that $I_{max}$ may vary from patient to patient due to changes in the amount of time that the electrode is in contact with the patient, the electrical characteristics of the patient's skin (i.e., resistivity, and the like), the amount of heat being conducted by the patient, the patient's initial skin temperature, and the like. With an electrosurgical return electrode designed according to the prior art, in the event that the contact area with the patient reduces below the $A_{contact(min)}$, while maintaining the $I_{max}$, a burn may result because $(I/A)_{critical} > 100 \ \text{mA/cm}^2$, which is the burn threshold. In contrast, the present invention limits the possibility of a burn caused from a reduction of the contact area below $A_{contact(min)}$, while also preventing electrosurgical procedures when the contact area is significantly reduced. Therefore, by selecting the appropriate impedance of return electrode 170, the current I is always reduced below $I_{max}$ when $A < A_{contact(min)}$.

Figure 7:
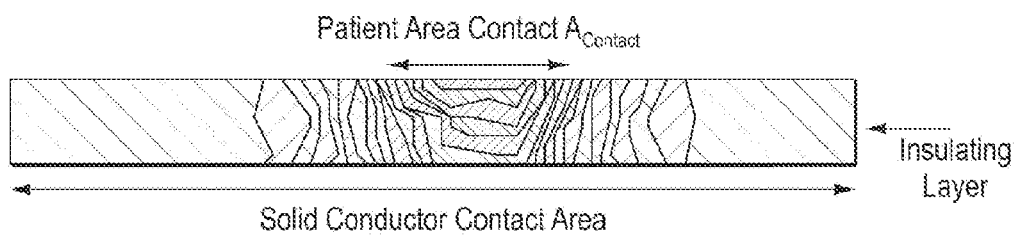
FIG. 7 is a view illustrating current flow density within the electrode when the effective patient contact area is much smaller than the total electrode area.

As such, the impedance between the small electrode with area $A_{contact(min)}$ and the larger metal foil is not simply:

$$R = \frac{\rho t}{A_{contact(min)}} \quad (14)$$

as current can flow through the areas not directly below the patient contact area $A_{contact(min)}$ (FIG. 7). Approximately 10-20% more current flows through the patient contact area $A_{contact}$ than one would expect if the total area of the insulating layer were $A_{contact(min)}$. Equivalently, the effective impedance of the electrode is 10-20% less than what one would normally expect if these edge effects were not present resulting in additional current flow.

As previously mentioned, FIG. 7 reveals current flow distribution through the semi-insulating part of the electrode when the upper contact area with the patient is much smaller than the total electrode surface area. As depicted, current flows through parallel paths around the contact region thus reducing the overall impedance to current flow and thereby increasing the effective area about 10-20 percent. In the Figure, the opaque or heavily hatched region denotes heavier current flow, and the lighter or lightly hatched region denotes lesser current flow.

In order for the electrode to be self-limiting, and as efficacious as defined by the AAMI standard, it is preferred that $A_{contact(min)}$ have a value from about 7 cm$^2$ to about 22 cm$^2$, and more preferably about 10 cm$^2$ for electrosurgical currents between 100 mA and about 2,000 mA. Similarly, it is preferred that $\beta$ range from about 10 to about 50, and more preferably have a value of about 10. Using the various values for $A_{contact(min)}$ and $\beta$, it is preferable to solve Equation 11 for the thickness t as a function of the bulk resistivity $\rho$ at different electrosurgical generator frequencies $\omega$, while inserting a factor of 1.2 to account for the edge effects described above. In the particular illustrative embodiment discussed herein, the factor of 1.2 is included within the resistivity and reactance terms of the equation; however, it may be appreciated by one skilled in the art that the factor of 1.2 is geometry dependent for both the resistive and reactance terms and may vary. Additionally, the value of 1.2 is based on the illustrative geometry of the presently described self-limiting electrode and may vary as the geometry of the electrode varies to account for the different edge effects.

The resulting equation (which identifies and defines the interrelationships of parameters affecting self-limitation) is:

$$t = \frac{1.2A(75\beta)\sqrt{1+\omega^2 \rho^2 \kappa^2 \varepsilon_0^2}}{\rho} \quad (15)$$

Figure 8:
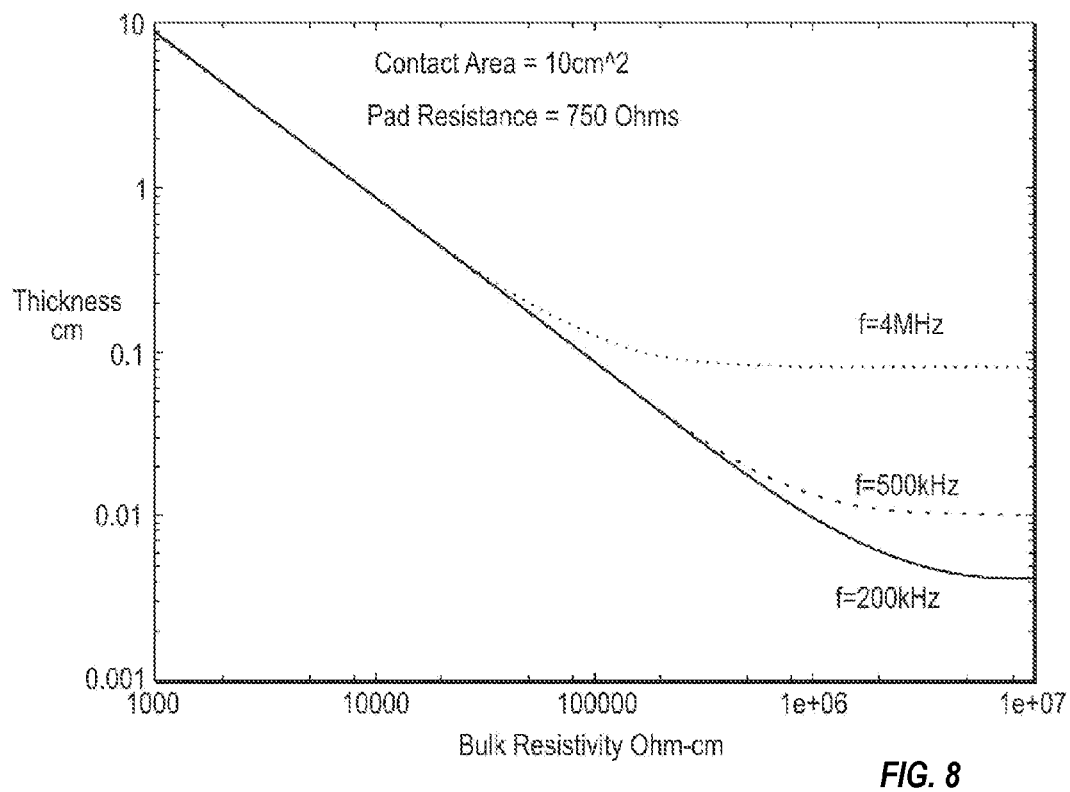
FIG. 8 is a graph depicting variations of bulk resistivity of a resistive layer as a function of electrode thickness for different electrosurgical generator frequencies.

Using Equation 15, FIG. 8 illustrates the variation of minimum bulk resistivity, with electrode thickness, requiring $\kappa=5$. The maximum electrode thickness one would imagine using would range from about 0.5 to about 4 inches (about 1.3 cm to about 10.2 cm) and more preferably about 1 inch thick (about 2.5 cm). Above these thicknesses, the electrode may become unwieldy to use and uncomfortable for the patient. Thus, to be self-limiting, the minimum bulk resistivity for an electrode of such thickness is about 4000 $\Omega \cdot$cm.

The preceding equations and discussion are representative of the bulk resistivity required for return electrode 170 (FIG.

6) to be self-limiting. It may be appreciated, however, that the above analysis may be repeated to obtain the necessary self-limiting impedances for electrodes modeled using primarily capacitive or inductive components, or combinations of resistive, capacitive, and/or inductive components. Therefore, following is a discussion of the self-limiting requirements for the bulk impedance of return electrode 170, whether such impedance arises from resistive, capacitive, and/or inductive components of impedance.

The self-limiting behavior of the return electrode of the present disclosure results from the existence of sufficient return impedance to make an electrode site burn impossible when the area of contact between the patient and the return electrode is substantially reduced. As shown above, the combination of the maximum electrosurgical currents of 1000 mA coupled with the requirement that the current density be kept below 100 mA/cm$^2$ yields a minimum safe contact area of 10 cm$^2$.

In general, this requirement can be met with any number of electronic components hooked together in various configurations, including series and parallel combinations of capacitors, resistors, and even inductors, provided that the total impedance presented by the resulting circuit be about 75β or greater when the contact area is reduced to 10 cm$^2$.

Define the total impedance of the circuit between the return electrode of the electrosurgical generator and the patient as $Z_{TOT}$. This impedance is generated by the capacitive, resistive, and inductive properties of the materials inserted between the patient and the return electrode. We define the "bulk impedance" of the material η, a volume independent measure of the impedance of the material, that is frequency dependent, as:

$$\eta = \frac{(A)(Z_{TOT})}{t} \quad (16)$$

Here A is the area of the material and t is the thickness. This is analogous to the relationship between the volume dependent ohmic resistance R and the related volume independent characteristic of the resistive material called the "bulk resistivity" ρ described earlier.

One manner to describe the self-limiting requirement is expressed in terms of η:

$$|Z_{TOT}| = \frac{t|\eta|}{A} > 75\beta \quad (17)$$

Or therefore $$|\eta| > \frac{(75\beta)A}{t} \quad (18)$$

For the previous case (minimum bulk resistivity specification) we used $A = A_{contact(min)} = 10$ cm$^2$, (about 1.55 inch$^2$), β=10, and $t = t_{max} = 1$ inch (about 2.5 cm), and a factor of 1.2 to account for edge effects to find that for a pure resistive return electrode, $$|\eta| > 4000 \; \Omega \cdot cm \quad (19)$$

Therefore, in the purely resistive case, the bulk impedance (η) is identified as the bulk resistivity (ρ) of the conducting material in the electrode. The results in Equation 19, however, generalize to all materials and electrical components, including resistive, capacitive, and inductive components, and any combinations thereof. As long as the bulk impedance of the return electrode is greater than 4000 Ω·cm, the return electrode will be self-limiting, regardless of whether the self-limiting behavior is due to a resistive, capacitive, inductive impedance, or any combination of these impedances.

As alternate illustrative examples, one might construct a self-limiting return electrode using a conductive/resistive return plate coated with an insulating (dielectric) material or one might construct a patient gown out of dielectric material and use a metallic or resistive return electrode. The total effect of these devices would be to create a resistive impedance in series with a capacitive impedance.

For the above defined illustrative examples that model the return electrode in terms of resistive and capacitive impedances, the total impedance of the return electrode is the sum of the resistive and the capacitive impedances, given by:

$$Z_{TOT} = R + \frac{1}{j\omega C} \quad (20)$$

In terms of the material bulk resistivity, dielectric constant, area, and thickness, the total impedance is:

$$Z_{TOT} = \frac{\rho t}{A} + \frac{t}{j\omega \kappa \varepsilon_0 A} \quad (21)$$

By multiplying both sides of the equation by the area A, and dividing by the thickness t, we can derive the bulk impedance η:

$$\eta = \rho + \frac{1}{j\omega \kappa \varepsilon_0} \quad (22)$$

The magnitude of the bulk impedance is:

$$|\eta| = \sqrt{\rho^2 + \frac{1}{(\omega \kappa \varepsilon_0)^2}} \quad (23)$$

If we require $$|\eta| > \frac{(75\beta)(1.2A)}{t} \quad (24)$$

Then $$\frac{A}{t} < \frac{|\eta|}{1.2(75\beta)} = \frac{\sqrt{\rho^2 + \frac{1}{(\omega \kappa \varepsilon_0)^2}}}{1.2(75\beta)} \quad (25)$$

As such, the edge effects reduce the bulk impedance of the return electrode by about 10-20 percent, thereby causing a corresponding increase in the effective area of the self-limiting return electrode by about 10-20 percent and reduce the possibility of unwanted electrosurgical burns.

Figure 9:
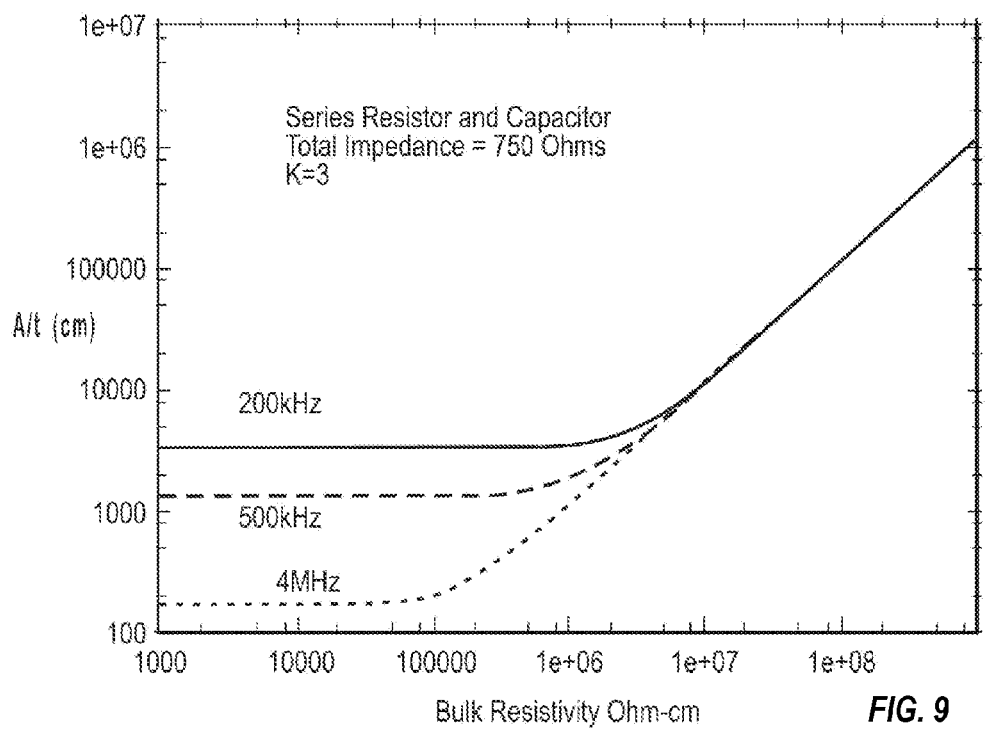
FIG. 9 is a graph showing bulk resistivity as a function of the area divided by the thickness of an electrosurgical return electrode in accordance with the present invention at various electrosurgical frequencies.

FIG. 9 plots A/t vs. bulk impedance η for various electrosurgical frequencies. The y axis has the minimum ratio of A/t in order to have self-limiting behavior as a function of the bulk impedance. Note that we require bulk impedance always greater than 4000 Ω·cm. On the right hand side of the plot, all of the curves merge into one. In this regime, the total impedance of the circuit is dominated by the resistive component and is, hence, independent of frequency. On the left hand side, the circuit impedance is dominated by the capacitive conduction of current. One requires area to thickness ratios of several hundred to about 10,000 in order to provide sufficient total impedance with the low ohmic resistance in this region.

As mentioned above, FIGS. 6-12 are set forth to define the geometries and characteristics of materials employed to obtain the foregoing self-limiting characteristics. Discussion will be made hereinafter to present illustrative information and an example related to a return electrode that may be used for electrosurgical procedures utilizing capacitive conduction while still remaining self-limiting. Although discussion is made herein with respect to a return electrode functioning under capacitive conduction, similar illustrative information and examples may be provided for resistive and inductive conduction, as known by one skilled in the art.

Figure 10:
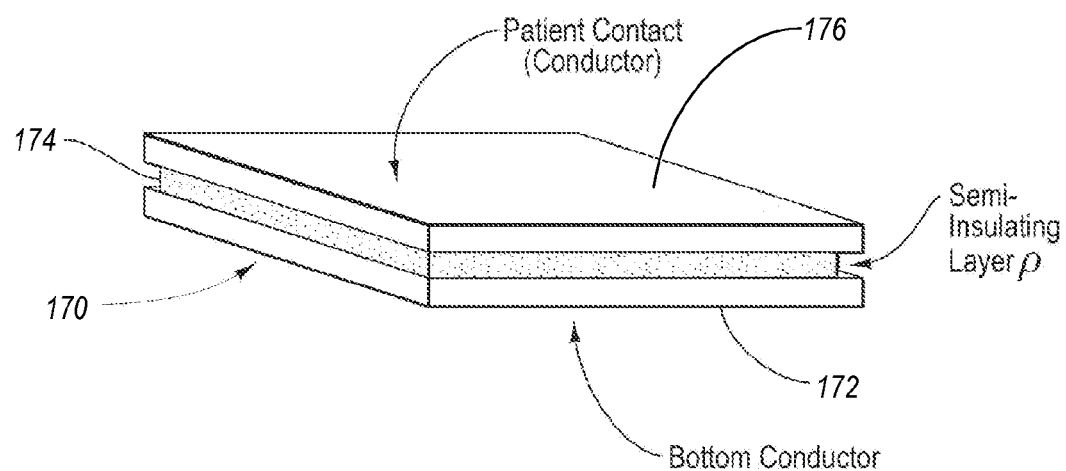
FIG. 10 is a perspective view illustrating, for the purpose of analysis, the circuit equivalent of a patient in operative association with the ohmic and capacitive regions of an electrode according to the invention.
Figure 11:
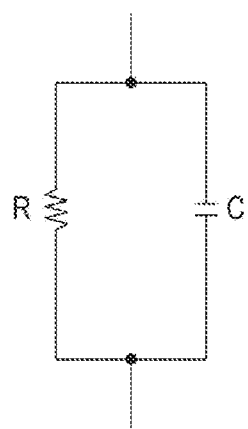
FIG. 11 is a simple electronic schematic circuit equivalent to FIG. 10.

FIG. 10 depicts return electrode 170 consisting of conductive metal backing 172 and a semi-insulating layer 174 of material with bulk resistivity $\rho$, thickness t and area A. The electrode is in contact with another conducting layer 176 that represents a patient thereupon. The circuit can be modeled as a resistor R in parallel with a capacitor C as illustrated in FIG. 11. The resistance R is related to the bulk resistivity $\rho$, area A, and thickness t by the formula:

$$R = \frac{\rho t}{A} \tag{26}$$

The capacitance C is approximately related to the area A, thickness t, permittivity constant $\varepsilon_0 = 8.85 \times 10^{-12}$ F/m, and the dielectric constant of the material $\kappa$, as follows:

$$C = \frac{\kappa \varepsilon_0 A}{t} \tag{27}$$

The magnitude of the capacitor impedance is:

$$X_C = \frac{1}{\omega C} = \frac{t}{\omega \kappa \varepsilon_0 A} \tag{28}$$

The ratio Y of the current flow due to the capacitive path to the current flow due to the resistive path is:

$$Y = \frac{\frac{1}{X_C}}{\frac{1}{R}} = \frac{\frac{\omega \kappa \varepsilon_0 A}{t}}{\frac{A}{\rho t}} = \omega \kappa \varepsilon_0 \rho \tag{29}$$

The ratio Y is independent of the electrode area and thickness, depending only upon $\kappa$ and $\rho$. For principally capacitive coupling, Y>>1, whereas for principally resistive current, Y<<1, the boundary between the capacitive current and the resistive current is Y=1.

$$1 = 2\pi f \kappa \varepsilon_0 \rho \tag{30}$$

We can use this, along with the value of $\varepsilon_0$, to find the necessary values of $\rho$ for capacitive conduction, given nominal values of $\kappa$ and $\omega = 2\pi f$ where f is the electrosurgical generator frequency.

$$\rho = \frac{1}{2\pi f \kappa \varepsilon_0} \tag{31}$$

For most insulating materials, $\kappa$ ranges from 3 to 5. Commercially available electrosurgical generators presently have operating frequencies ranging from 200 kHz to 4 MHz. For $\kappa=5$ and f=4 MHz, it is preferred that $\rho \geq 1 \times 10^5$ $\Omega \cdot$cm for the electrosurgical electrode to return the majority of its current through capacitive coupling. For $\kappa=3$ and f=200 kHz, we require $\rho \geq 3 \times 10$ $\Omega \cdot$cm.

The percentage of total current derived through capacitive coupling is given by:

$$\text{pct} = \frac{\frac{1}{|X_C|^2}}{\frac{1}{|R|^2} + \frac{1}{|X_C|^2}} = \frac{|R|^2}{|R|^2 + |X_C|^2} = \frac{\left(\frac{\rho t}{A}\right)^2}{(\rho t)^2 + \left(\frac{t}{A \varepsilon_0 \kappa \omega}\right)^2} \tag{32}$$

$$= \frac{\rho^2}{\rho^2 + \left(\frac{1}{\varepsilon_0 \kappa \omega}\right)^2} = \frac{(\varepsilon_0 \kappa \omega \rho)^2}{(\varepsilon_0 \kappa \omega \rho)^2 + 1}$$

Figure 12:
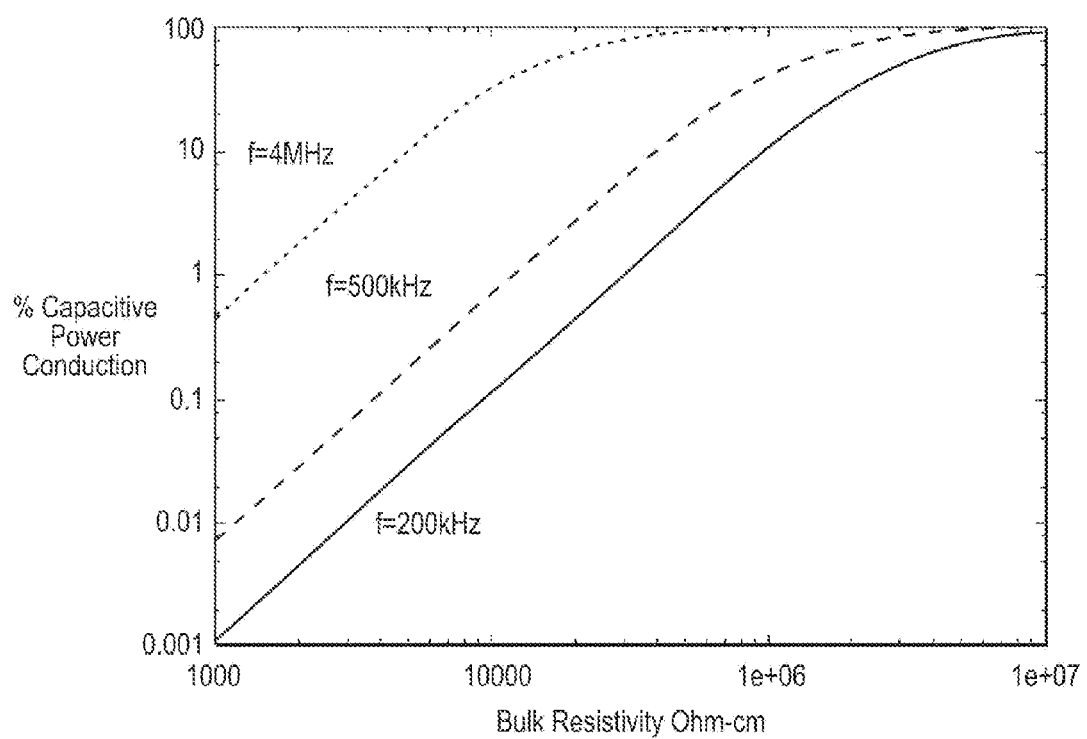
FIG. 12 is a graph depicting percent capacitive power conduction as a function of bulk resistivity of the resistive layer for different electrosurgical operating frequencies.

FIG. 12 illustrates the percentage (%) of capacitive coupling for various frequency electrosurgical generators. At the extreme (4 MHz), a minimum bulk impedance of $10^5$ $\Omega \cdot$cm is required for the majority of the current to be passed through capacitive coupling.

Figure 13:
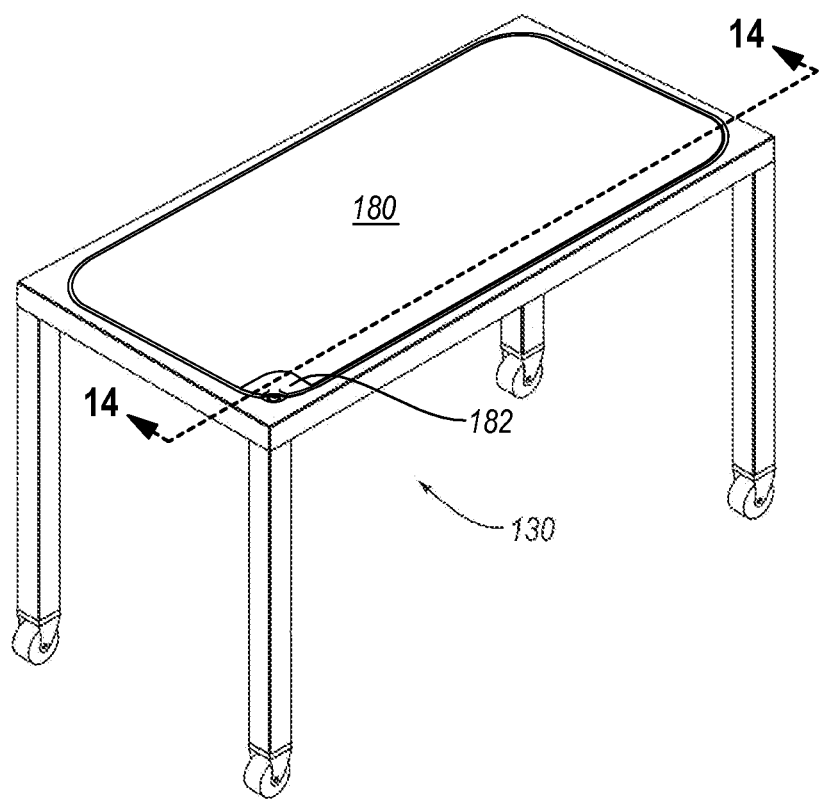
FIG. 13 is a perspective view showing an operating table with an electrosurgical return electrode according to the present disclosure disposed on the upper surface thereof.

Attention is now directed to FIGS. 13-16, which illustrate an electrosurgical return electrode 180 according to the present disclosure. FIG. 13 illustrates return electrode 180 on operating table 130. Similar to return electrode 132, return electrode 180 includes an electrical connector 182 to provide a conventional electrical return to the electrosurgical radio frequency energy source.

FIG. 14 illustrates a simplified section taken along the lines 14-14 of FIG. 13 and FIG. 15 illustrates an exploded view of return electrode 180. As illustrated in FIGS. 14 and 15, return electrode 180 includes a conductive element 184 and pads 186, 188 on opposing sides of conductive element 184. Conductive element 184, in one configuration, may be similar to conductive element 140. Nevertheless, it may be appreciated by one skilled in the art that conductive element 184 may have various other configurations so long as conductive element 184 is capable of performing the functions of an electrode, i.e., being capable of passing current therethrough.

Referring again to FIGS. 14 and 15, disposed on opposing sides of conductive element 184 are pads 186, 188. As can be seen, pad 186 has an outer cover layer 190 and an inner cover layer 192 that define an interior chamber 194 therebetween. Outer cover layer 190 is configured to be placed against the surface of a patient (thereby acting as a working surface of return electrode 180), while inner cover layer 192 is disposed next to conductive element 184. In some embodiments, inner cover layer 192 is secured to conductive element 184, such as with an adhesive, to prevent air bubbles or separation between pad 186 and conductive element 184. Outer and inner cover layers 190, 192 may be formed individually and secured together about their edges or may be integrally formed. Outer and inner cover layers 190, 192 may be formed of various materials, such as urethane. A fill material 196, discussed elsewhere herein, may be disposed in interior chamber 194.

Similar to pad 186, pad 188 includes an outer cover layer 198 and a fill material 200. Outer cover layer 198 is configured to be placed against the surface of a patient (thereby acting as a second working surface of return electrode 180), while fill material 200 is disposed next to conductive element 184. Like outer and inner cover layers 190, 192, outer cover layer 198 may be formed of various materials, such as urethane.

Rather than having a second inner cover layer, pad 188 may be formed during the assembly of return electrode 180. For instance, during assembly of return electrode 180, chamber 194 in pad 186 may be filled with material 196 and sealed closed such that material 196 cannot escape from chamber 194. Pad 186 may be disposed next to and/or secured to a first major surface of conductive element 184. The edges of outer cover layer 198 may then be secured to the edges of pad 186 so as to create a chamber between conductive element 184 and outer cover layer 198. The newly defined chamber may then be filled with material 200 and sealed closed to retain material 200 therein.

It will be appreciated that pads 186, 188 may similar or identical to one another. For instance, in addition to outer cover layer 198 and material 200, pad 188 may also include an inner cover layer (similar to inner cover layer 192) that cooperates with outer cover layer 198 to define a chamber for receiving material 200. Furthermore, pad 188 may also be secured to conductive element 184. For instance, in embodiments where pad 188 includes an inner cover layer, the inner cover layer may be secured, such as with an adhesive, to a second major surface of conductive element 184. Likewise, pad 186 may be similar to pad 188 in that pad 186 may be formed without inner cover layer 192.

The materials forming return electrode 180, conductive element 184, and pads 186, 188, control the passage of current from a patient to conductive element 184. As such, in one embodiment, pads 186, 188 and fill materials 196, 200 are insulative, while in an alternate configuration pads 186, 188 and/or materials 196, 200 may be conductive and aid in the passage of current from the patient to conductive element 184. So long as return electrode 180 provides the self-limiting characteristics described herein, the various elements of return electrode 180, i.e., conductive element 184 and pads 186, 188, may provide one or more resistive, inductive, and/or capacitive inductance components to the bulk impedance.

In addition to the materials used to form pads 186, 188, the thickness of pads 186, 188 can affect the transmission of current from a patient to conductive element 184. By way of non-limiting example, forming pads 186, 188 relatively thin can facilitate capacitive coupling between conductive element 184 and a patient resting upon return electrode 180. Through this capacitive coupling, current used during electrosurgery is passed from the patient to return electrode 180. As will be understood by one of ordinary skill in the art in light of the disclosure herein, the capacitive coupling between the patient and return electrode 180 can be directly related to the self-limiting characteristics of return electrode 180. Thus, making pads 186, 188 relatively thin contributes to good electrical coupling between the patient and return electrode 180 so as to enable safe and effective electrosurgery for substantially any sized patient. Accordingly, each of pads 186, 188 may each have a thickness within a predetermined range. For instance, in some embodiments, each of pads 186, 188 has an approximate thickness of between about 0.02 inches to about 0.120 inches, giving the return electrode 180 a total thickness of about 0.135 inches.

The inclusion of pads 186, 188, which are substantially similar to one another, on opposing sides of conductive element 184 provides return electrode 180 with a substantially symmetrical construction. The symmetrical nature of return electrode 180 provides return electrode 180 with two surfaces that function as working surfaces. More specifically, the major surfaces of return electrode 180 defined by outer cover layers 192, 198 may each be used as a working surface. For instance, return electrode may be positioned so that outer cover layer 192 is positioned towards a patient and return electrode 180 will exhibit the self-limiting characteristics discussed herein. Likewise, return electrode 180 can be turned over so that outer cover layer 198 is positioned against a patient and return electrode 180 will exhibit the self-limiting characteristics discussed herein.

As discussed elsewhere herein, previous return electrodes were made for specific categories of patients. The categories were typically defined by patient weight ranges (e.g., less than 5 kg, 5 kg to 15 kg, and over 15 kg). In addition to selecting the proper return electrode based on the patient's weight, operating room personnel also needed to ensure that power settings on the electrosurgical generator were set in accordance with the restrictions associated with the particular return electrode used (e.g., to limit current to: 350 mA for patients under 5 kg; 500 mA for patients between 5 kg and 15 kg; and 700 mA for patients over 15 kg). Selecting the correct return electrode and making sure that the settings of the electrosurgical generator were properly set could be confusing and viewed as trivial matters for operating room personnel, especially those not familiar with the principles of electricity.

In contrast, return electrode 180 functions with patients of substantially any size. For instance, in one implementation, return electrode 180 may be used with patients that weigh 0.8 lb or more. In another implementation, return electrode 180 may be used with patients from multiple industry standard weight categories. For instance, return electrode 180 may be used on any patient regardless of whether that patient falls within IEC's less than 5 kg category, 5 kg to 15 kg category, or above 15 kg category. Furthermore, since return electrode 180 can be used with substantially any sized patient, operating personnel do not have to limit or adjust the generator power settings to accommodate different return electrodes.

Figure 16:
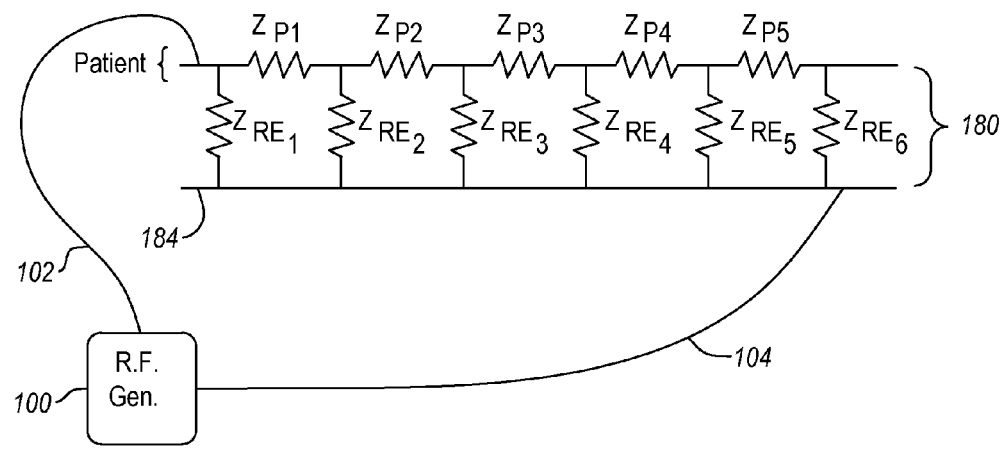
FIG. 16 is a simplified electrical schematic diagram illustrating typical resistances encountered by radio frequency current during an operative procedure with the electrode of FIG. 13.

As noted elsewhere herein, return electrode 132 discussed above is designed based on the assumption that patients are purely conductive. In contrast, return electrode 180 is designed with the understanding that patients are both conductive and resistive. FIG. 16 illustrates a simplified electrical schematic diagram of a patient lying on return electrode 180 and electrical conductors 102 and 104 electrically connecting the patient and return electrode 180 to generator 100.

Generally, the patient and conductive element 184 may be thought of as opposing plates of a parallel capacitor. Unlike the plates from traditional parallel plate capacitors, however, the patient is not purely conductive. Rather, as illustrated in FIG. 16, the patient is both conductive and resistive. In particular, portions of the patient are conductive while other portions of the patient (represented by $Z_{P1}$-$Z_{P5}$) are resistive. Thus, when electrosurgical current is transmitted from generator 100 to the patient via conductor 102, the resistive portions of the patient will resist spread of the electrosurgical current through the patient.

To accommodate for the fact that the patient's own resistance will resist the even spread of the electrosurgical current throughout the patient, return electrode 180 is designed to allow for the non-uniform transfer of the electrosurgical current from the patient to conductive element 184. More specifically, return electrode 180 is designed to allow for more current to be transmitted from the patient to conductive element 184 near the surgical site than away from the surgical site while still providing the self-limiting characteristics discussed herein.

Return electrode 180 has resistive properties that resist the transfer of current from the patient to conductive element 184. As illustrated in FIG. 16, the resistance presented by return electrode 180 may be conceptually thought of as individual resistors $Z_{RE1}$-$Z_{RE6}$, each of which is associated with an area of return electrode 180. Nevertheless, it will be understood that return electrode 180 may not necessarily formed of individual resistors, but electrically return electrode 180 may function as though it were.

During an electrosurgical procedure, conductor 102 may transmit electrosurgical current to the patient is the area of patient illustrated in FIG. 16. As the current begins to spread through the patient, the current will encounter the resistance $Z_{P1}$ presented by some of the patient's tissue. Because of the resistance provided by $Z_{P1}$, the current will seek an alternate path, which is presented by $Z_{RE1}$ of return electrode 180. The values of $Z_{P1}$ and $Z_{RE1}$ will determine how much of the current will spread to other portions of the patient (e.g., through $Z_{P1}$) and how much of the current will be transmitted to conductive element 184. At least some of the current will pass through $Z_{P1}$ and encounter $Z_{P2}$ presented by patient tissue and $Z_{RE2}$ presented by return electrode 180. Again, the values of each will determine how much current passes through each of $Z_{P2}$ and $Z_{RE2}$. This process will continue throughout the portion of the patient that is in contact with return electrode 180.

Materials and geometries may be selected for return electrode 180 so that the resistance presented by return electrode will allow more current to be transmitted from the patient to conductive element 184 near the surgical site as opposed to requiring an even distribution of the current being transmitted therebetween. By way of example, limiting the thickness of pads 186, 188 to below about 0.120 inches can enable return electrode 180 to present a level of resistance that allows for uneven distribution of current being transferred from a patient to conductive element 184. For instance, return electrode 180 can be configured to allow more current to be transferred through $Z_{RE1}$ than through $Z_{RE2}$, and more current through $Z_{RE2}$ than through $Z_{RE3}$, and so on. Furthermore, restraining the thickness of pads 186, 188 can also facilitate improved capacitive coupling between conductive element 184 and patients of substantially any size, thereby allowing return electrode 180 to be safely used with patients of substantially any size.

In addition or as an alternative to adjusting the thickness of pads 186, 188 (e.g., limiting the thickness to about 0.120 inches or less), the dielectric constants of the materials used in pads 186, 188 may be adjusted to achieve the desired level of capacitive coupling and/or resistance presented by return electrode 180. As noted above (see Equation 27), the capacitance between the patient and the conductive element 184 is dependent on the thickness of the pad (e.g., pads 186, 188) therebetween, the amount of contact area between the patient and return electrode 180, as well as the dielectric constants of the pad materials. Accordingly, the materials used to form pads 186, 188 may be selected, as least in part, based upon the value of their dielectric constants. Similarly, the materials used in pads 186, 188 may be altered (e.g., by doping) to adjust their dielectric constants in order to provide the desired capacitance and/or resistance.

It will now be evident that there have been described herein improved universal electrosurgical return electrodes. The disclosed universal return electrodes are more versatile than prior return electrodes. For instance, the improved return electrodes are safely usable across multiple categories of patients. Thus, rather than needing different sized return electrodes for different sized patients, the improved return electrodes disclosed herein can be used with substantially any sized patient (e.g., 0.8 lbs. and above). Furthermore, because the disclosed return electrodes can be safely used with substantially any sized patient, operating room personnel do not have to adjust the settings of an electrosurgical generator according to the limitations of different return electrodes (e.g., different sized sticky pads). Additionally, some of the improved return electrodes disclosed herein provide multiple working surfaces. As a result, the return electrode can be placed with either major surface toward a patient and the return electrode will perform as desired. Making both major surfaces of the return electrode function as working surfaces eliminates the risk that a non-working surface will be placed against a patient during a surgical procedure.

The terms "approximately," "about," and "substantially" as used herein represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of a stated amount.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A universal safety electrosurgical return electrode comprising:
   a conductive element configured to conduct electrical current, the conductive element having opposing first and second major surfaces;
   a first pad positioned adjacent the first major surface of the conductive element, wherein the first pad has a thickness of greater than 0.0 inches and up to 0.120 inches; and
   a second pad positioned adjacent the second major surface of the conductive element, wherein the second pad has a thickness of greater than 0.0 inches and up to 0.120 inches,
   wherein the universal safety electrosurgical return electrode is configured to have a patient contact a portion of either the first pad or the second pad during an electrosurgical procedure, wherein electrical current can be transferred between the patient and the conductive element through whichever of the first pad or the second pad is disposed between the patient and the conductive element, and wherein the size of, arrangement of, or materials forming the conductive element, the first pad, or the second pad of the universal safety electrosurgical return electrode is configured such that electrical current transferred from the patient to the conductive element is transmitted non-uniformly over the portion of the universal safety electrosurgical return electrode that is contacted by the patient, and wherein the thicknesses of the first and second pads and the resulting non-uniform transfer of electrical current are configured to enable the universal safety electrosurgical return electrode to be self-limiting to maintain current densities below a threshold level when used with any patient that weighs 0.8 lbs. or more.

2. A universal safety electrosurgical return electrode according to 1, wherein the first pad defines an outer surface configured to be positioned adjacent a patient during an electrosurgical procedure, wherein a first portion of the conductive element is disposed closer to the outer surface than a second portion of the conductive element.

3. A universal safety electrosurgical return electrode accordingly to claim 1, wherein the conductive element has a generally arch or dome shape.

4. A universal safety electrosurgical return electrode according to claim 1, wherein the first and second pads are configured to cooperate with the conductive element to define first and second working surfaces on opposing sides of the universal safety electrosurgical return electrode.

5. A universal safety electrosurgical return electrode according to claim 4, wherein the universal safety electrosurgical return electrode is configured to have either the first working surface or the second working surface positioned toward a patient during an electrosurgical procedure.

6. A universal safety electrosurgical return electrode according to claim 1, wherein each of (i) the first pad and the conductive element and (ii) the second pad and the conductive element are configured to limit the density of current flowing through the universal safety electrosurgical return electrode to below 100 mA/cm$^2$.

7. A universal safety electrosurgical return electrode according to claim 1, wherein at least one of the first and second pads is formed of a gel.

8. A universal safety electrosurgical return electrode according to claim 1, wherein the first and second pads are configured to be secured to one another with the conductive element therebetween.

9. A universal safety electrosurgical return electrode according to claim 1, wherein each of the first pad and the second pad has a thickness between 0.02 inches and 0.120 inches.

10. A universal safety electrosurgical return electrode according to claim 1, wherein at least one of the first and second pads comprises an inner cover layer and an outer cover layer that define an interior chamber filled with a fill material.

11. A reversible safety electrosurgical return electrode comprising:
a conductive element configured to conduct electrical current, the conductive element having a first planar major surface and an opposing second planar major surface;
a first pad positioned adjacent the first planar major surface of the conductive element, wherein the reversible safety electrosurgical return electrode has a first exterior working surface on a side of the first pad opposite to the conductive element, the first exterior working surface being disposed on a first side of the reversible safety electrosurgical return electrode and facing away from the conductive element, the first exterior working surface being configured to transfer electrical current between a patient positioned adjacent to the first exterior working surface and the conductive element during an electrosurgical procedure; and
a second pad positioned adjacent the second planar major surface of the conductive element, wherein the reversible safety electrosurgical return electrode has a second exterior working surface on a side of the second pad opposite to the conductive element, the second exterior working surfacing being disposed on a second side of the reversible safety electrosurgical return electrode opposite to the first side and facing away from the conductive element and the first pad, the second exterior working surface being configured to transfer electrical current between a patient positioned adjacent to the second exterior working surface and the conductive element during an electrosurgical procedure,
wherein the reversible electrosurgical return electrode is configured to have either the first exterior working surface or the second exterior working surface positioned toward a patient during an electrosurgical procedure such that electrical current can be transferred between a patient and the conductive element through either the first exterior working surface or the second exterior working surface.

12. A reversible safety electrosurgical return electrode according to claim 11, wherein the first pad comprises an inner cover layer and an outer cover layer that define an interior chamber.

13. A reversible safety electrosurgical return electrode according to claim 12, wherein the interior chamber is filled with a material selected from the group consisting of a visco-elastic material, a gel, water, saline, a water based material, a conductive oil, or combinations thereof.

14. A reversible safety electrosurgical return electrode according to claim 12, wherein the inner cover layer is secured to the first planar major surface of the conductive element.

15. A reversible safety electrosurgical return electrode according to claim 11, wherein the second pad comprises an outer cover layer and a fill material.

16. A reversible safety electrosurgical return electrode according to claim 15, wherein edges of the outer cover layer of the second pad are attached to edges of the first pad with the conductive element disposed between the first and second pads.

17. A reversible safety electrosurgical return electrode according to claim 15, wherein the outer cover layer of the second pad and the conductive element at least partially define a second interior chamber in which the fill material of the second pad is disposed.

18. A reversible safety electrosurgical return electrode according to claim 11, wherein the reversible safety electrosurgical return electrode is configured to have a patient contact a portion of either the first exterior working surface or the second exterior working surface during an electrosurgical procedure, and wherein the size of, arrangement of, or materials forming the conductive element, the first pad, or the second pad of the reversible safety electrosurgical return electrode is configured such that electrical current transferred from the patient to the conductive element is transmitted non-uniformly over the portion of the reversible safety electrosurgical return electrode that is contacted by the patient.

19. A reversible safety electrosurgical return electrode according to claim 11, wherein each of the first pad and the second pad has a thickness between 0.02 inches and 0.120 inches.

20. A reversible safety electrosurgical return electrode according to claim 11, wherein the reversible safety electrosurgical return electrode is configured to transfer electrical current between patients from multiple industry standard weight categories and the conductive element without risk of creating patient burns.

21. A universal safety electrosurgical return electrode comprising:
a conductive element configured to conduct electrical current, the conductive element having a first major surface, an opposing second major surface, and a predefined curved configuration;
a first pad positioned adjacent the first major surface of the conductive element, wherein the first pad has an inner surface disposed adjacent to the first major surface of the conductive element such that the inner surface and the first major surface face one another, the first pad also having a generally planar major outer surface configured to be positioned adjacent a patient during an electrosurgical procedure, the generally planar major outer surface being configured to transfer electrical current between a patient positioned adjacent to the generally planar major outer surface and the conductive element during an electrosurgical procedure; and
a second pad positioned adjacent the second major surface of the conductive element,
wherein the conductive element is secured between the first and second pads in the predefined curved configuration such that the first major surface of the conductive element is positioned closer to the generally planar major outer surface of the first pad in a first region of the universal safety electrosurgical return electrode than in a second region of the universal safety electrosurgical return electrode, wherein the curved configuration of the conductive element is configured to transfer more electrical current between the patient and the conductive element in the first region than between the patient and the conductive element in the second region, such that the electrical current transferred from the patient to the conductive element is transmitted non-uniformly over the portion of the universal safety electrosurgical return electrode that is contacted by the patient;
wherein the curved configuration of the conductive element and the resulting non-uniform transmission of electrical current enables the universal safety electrosurgical return electrode to be self-limiting to maintain current densities below a threshold level when used with any patient that weighs 0.8 lbs. or more.

22. A universal safety electrosurgical return electrode according to claim 21, wherein the first portion of the conductive element is positioned between 0.02 inches and 0.120 inches from the outer surface of the first pad.

23. A universal safety electrosurgical return electrode comprising:
a conductive element configured to conduct electrical current, the conductive element having a first major surface and an opposing second major surface;
a first pad positioned adjacent the first major surface of the conductive element, the first pad having an outer surface configured to be positioned adjacent a patient during an electrosurgical procedure, the outer surface being configured to transfer electrical current between a patient positioned adjacent to the outer surface and the conductive element during an electrosurgical procedure, the first pad having a first area having a first predefined dielectric constant and a second area having a second predefined dielectric constant, the first predefined dielectric constant being different than the second predefined dielectric constant, wherein the differing first and second predefined dielectric constants are configured to transfer more electrical current between the patient and the conductive element in the first area than between the patient and the conductive element in the second area, such that the electrical current transferred from the patient to the conductive element is transmitted non-uniformly over the portion of the universal safety electrosurgical return electrode that is contacted by the patient; and
a second pad positioned adjacent the second major surface of the conductive element,
wherein first and second predefined dielectric constants of the first pad and the resulting non-uniform transmission of electrical current enables the universal safety electrosurgical return electrode to be self-limiting to maintain current densities below a threshold level when used with any patient that weighs 0.8 lbs. or more.

24. A universal safety electrosurgical return electrode according to claim 23, wherein the second pad has an outer surface configured to be positioned adjacent a patient during an electrosurgical procedure.

25. A universal safety electrosurgical return electrode according to claim 23, wherein the second pad has a first area having a third predefined dielectric constant and a second area having a fourth predefined dielectric constant, the third predefined dielectric constant being different than the fourth predefined dielectric constant.

* * * * *